(12) United States Patent
Tatsuta et al.

(10) Patent No.: US 11,160,438 B2
(45) Date of Patent: Nov. 2, 2021

(54) ENDOSCOPE DEVICE AND MEASUREMENT SUPPORT METHOD

(71) Applicant: FUJIFILM Corporation, Tokyo (JP)

(72) Inventors: Takeichi Tatsuta, Kanagawa (JP);
Shinichiro Sonoda, Kanagawa (JP);
Issei Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 74 days.

(21) Appl. No.: 16/703,635

(22) Filed: Dec. 4, 2019

(65) Prior Publication Data

US 2020/0107698 A1 Apr. 9, 2020

Related U.S. Application Data

(63) Continuation of application No. PCT/JP2018/014389, filed on Apr. 4, 2018.

(30) Foreign Application Priority Data

Jul. 18, 2017 (JP) .............................. JP2017-139095

(51) Int. Cl.
*A61B 1/00* (2006.01)
*A61B 1/06* (2006.01)
(Continued)

(52) U.S. Cl.
CPC ........ *A61B 1/0005* (2013.01); *A61B 1/00009* (2013.01); *A61B 1/0661* (2013.01);
(Continued)

(58) Field of Classification Search
CPC . A61B 1/0005; A61B 1/00009; A61B 1/0661; H04N 5/2254; H04N 5/2256; H04N 7/183

See application file for complete search history.

(56) References Cited

U.S. PATENT DOCUMENTS

| 4,980,763 A | 12/1990 | Lia |
| 2010/0217075 A1 | 8/2010 | Shigeta |
| 2016/0287141 A1 | 10/2016 | Sidlesky |

FOREIGN PATENT DOCUMENTS

| DE | 362469 C | 10/1922 |
| JP | S53-80285 U | 7/1978 |

(Continued)

OTHER PUBLICATIONS

English translation JP H3-128043 , May 1991.*
(Continued)

*Primary Examiner* — Mohammed S Rahaman
(74) *Attorney, Agent, or Firm* — Studebaker & Brackett PC

(57) ABSTRACT

An endoscope device includes a signal processing unit that processes a captured image signal, which is obtained by imaging a subject through an imaging optical system including an objective lens of an endoscope, to generates captured image, an auxiliary measurement light emitting unit that emits planar auxiliary measurement light from the distal end part, a display control unit that causes a display unit to display the captured image including an intersection line formed in a portion where a plane formed by the auxiliary measurement light intersects the subject. The auxiliary measurement light emitting unit emits the auxiliary measurement light in a state where the plane and an optical axis intersects each light at one specific point on the optical axis of the objective lens. A distance from a distal end part of the objective lens of the one specific point is 5 mm or more and 20 mm or less.

23 Claims, 14 Drawing Sheets

(51) Int. Cl.
*H04N 5/225* (2006.01)
*H04N 7/18* (2006.01)

(52) U.S. Cl.
CPC ......... *H04N 5/2254* (2013.01); *H04N 5/2256* (2013.01); *H04N 7/183* (2013.01)

(56) References Cited

FOREIGN PATENT DOCUMENTS

| JP | S6249208 A | | 3/1987 | | |
|---|---|---|---|---|---|
| JP | S6273223 A | | 4/1987 | | |
| JP | H02-85706 A | | 3/1990 | | |
| JP | H0313805 A | * | 1/1991 | ............... | H04N 7/18 |
| JP | H0313805 A | | 1/1991 | | |
| JP | H3-128043 | * | 5/1991 | ............... | H04N 7/18 |
| JP | H03128043 A | | 5/1991 | | |
| JP | H0412724 A | | 1/1992 | | |
| JP | H04-145313 A | | 5/1992 | | |
| JP | H04145313 | * | 5/1992 | ............... | H04N 7/18 |
| JP | 2008-194156 A | | 8/2008 | | |
| JP | 2009297435 A | | 12/2009 | | |
| JP | 2016-95458 A | | 5/2016 | | |
| JP | 2016-209342 A | | 12/2016 | | |
| JP | 2017508529 A | | 3/2017 | | |
| WO | 2009/084345 A1 | | 7/2009 | | |

OTHER PUBLICATIONS

The extended European search report issued by the European Patent Office dated Jun. 15, 2020, which corresponds to European Patent Application No. 18835490.6-1122 and is related to U.S. Appl. No. 16/703,635.

An Office Action; "Notice of Reasons for Refusal," mailed by the Japanese Patent Office dated Jan. 19, 2021, which corresponds to Japanese Patent Application No. 2019-530875 and is related to U.S. Appl. No. 16/703,635; with English language translation.

International Search Report issued in PCT/JP2018/014389; dated Jun. 26, 2018.

Written Opinion issued in PCT/JP2018/014389; dated Jun. 26, 2018.

An Office Action mailed by China National Intellectual Property Administration dated Jun. 3, 2021, which corresponds to Chinese Patent Application No. 201880039620.2 and is related to U.S. Appl. No. 16/703,635; with English language translation.

An Office Action; "Notice of Reasons for Refusal," mailed by the Japanese Patent Office dated Aug. 31, 2021, which corresponds to Japanese Patent Application No. 2019-530875 and is related to U.S. Appl. No. 16/703,635; with English language translation.

* cited by examiner

100 GB 2
ENDOSCOPE DEVICE AND MEASUREMENT SUPPORT METHOD

CROSS-REFERENCE TO RELATED APPLICATIONS

This application is a Continuation of PCT International Application No. PCT/JP2018/014389 filed on Apr. 4, 2018, which claims priority under 35 U.S.C. § 119(a) to Japanese Patent Application No. 2017-139095 filed on Jul. 18, 2017. Each of the above application(s) is hereby expressly incorporated by reference, in its entirety, into the present application.

BACKGROUND OF THE INVENTION

1. Field of the Invention

The present invention relates to an endoscope device and a measurement support method.

2. Description of the Related Art

In endoscope devices, measuring the distance to an object to be observed or the size of the object to be observed is performed.

For example, JP1992-012724A (JP-H04-012724A) discloses an endoscope device that sweeps the planar light from a distal end of an endoscope and processing a captured image obtained by imaging an observation region in a state where the planar light is swept, thereby obtaining three-dimensional information on an object to be observed irradiated with planar light.

Additionally, JP2017-508529A discloses an endoscope device that irradiates planar light from a distal end of an endoscope and displays a mesh line indicating the track of the planar light and a curved line where the planar light intersects an object to be observed in an overlapping manner on a captured image. In this endoscope device, in a case where two points on the curved line overlapping the captured image are selected, the distance between the two points is calculated and displayed.

SUMMARY OF THE INVENTION

The endoscope device according to JP1992-012724A (JP-H4-012724A) and JP2017-508529A emits planar light into a visual field of the objective optical system of the endoscope. However, distortion occurs at a peripheral part of the visual field of the objective optical system of the endoscope. For this reason, it is difficult to accurately perform the measurement of the object to be observed in a state where the planar light is irradiated to the periphery of the visual field of the objective optical system of the endoscope.

Additionally, in the visual field of the objective optical system of the endoscope, an observation range, which is a range in the direction of an optical axis on which a subject can be focused and sufficient resolution can be obtained, is present. For this reason, in a state where the planar light for measurement is not emitted into the observation range, the measurement of the object to be observed cannot be accurately performed.

Additionally, an optimal observation range particularly suitable for observing the subject is present in the observation range of the endoscope. An endoscope user often performs the operation of adjusting a distal end position of the endoscope such that the object to be observed, such as a polyp, falls within the optimal observation range.

Additionally, the endoscope user often performs the operation of adjusting the distal end position of the endoscope such that the object to be observed is as close to the center of the captured image as possible (in other words, such that the object to be observed is on the optical axis of the objective optical system) from a relationship of the distortion of the periphery of the visual field of the above-described objective optical system.

Hence, the user needs to emit the planar light for measurement into the visual field of the objective optical system in consideration of the operation performed at high frequency.

JP1992-012724A (JP-H4-012724A) and JP2017-508529A do not disclose how the planar light is to be emitted to the visual field of the objective optical system.

Additionally, in the method of sweeping the planar light described in JP1992-012724A (JP-H4-012724A) and JP2017-508529A, the structure of the distal end of the endoscope and the image processing become complicated, and the manufacturing cost of the endoscope devices increases.

The invention has been made in view of the above circumstances, and an object thereof is to provide an endoscope device and a measurement support method that can accurately measure an object to be observed, and can prevent an increase in the manufacturing cost of an endoscope.

An endoscope device of the invention comprises an imaging optical system including an objective lens disposed at a distal end part of an endoscope; an imaging element that images a subject through the imaging optical system; a signal processing unit that processes a captured image signal obtained by imaging a subject by the imaging element to generate a captured image; an auxiliary measurement light emitting unit that emits planar auxiliary measurement light from the distal end part; and a display control unit that causes a display unit to display the captured image including an intersection line between the auxiliary measurement light and the subject that is formed in a portion where a plane formed by the auxiliary measurement light intersects the subject. The auxiliary measurement light emitting unit emits the auxiliary measurement light in a state where the plane and an optical axis of the objective lens intersect each other at one specific point on the optical axis of the objective lens. A distance of the one specific point from a distal end part of the objective lens is 5 mm or more and 20 mm or less.

A measurement support method of the invention comprises a signal processing step of processing a captured image signal, which is obtained by imaging a subject by an imaging element through an imaging optical system including an objective lens disposed at a distal end part of an endoscope, to generate a captured image; an auxiliary measurement light emission control step of causing planar auxiliary measurement light to be emitted from the distal end part; and a display control step of causing a display unit to display the captured image including an intersection line between the auxiliary measurement light and the subject that is formed in a portion where a plane formed by the auxiliary measurement light intersects the subject. In the auxiliary measurement light emission control step, the auxiliary measurement light is caused to be emitted from the distal end part in a state where an optical axis of the objective lens and the plane intersect each other at one specific point on the optical axis. A distance of the one specific point from a distal end part of the objective lens is 5 mm or more and 20 mm or less.

According to the invention, it is possible to provide an endoscope device and a measurement support method that can accurately measure an object to be observed, and can prevent an increase in the manufacturing cost of an endoscope.

DESCRIPTION OF THE PREFERRED EMBODIMENTS

Hereinafter, embodiments of the invention will be described with reference to the drawings.

Figure 1:
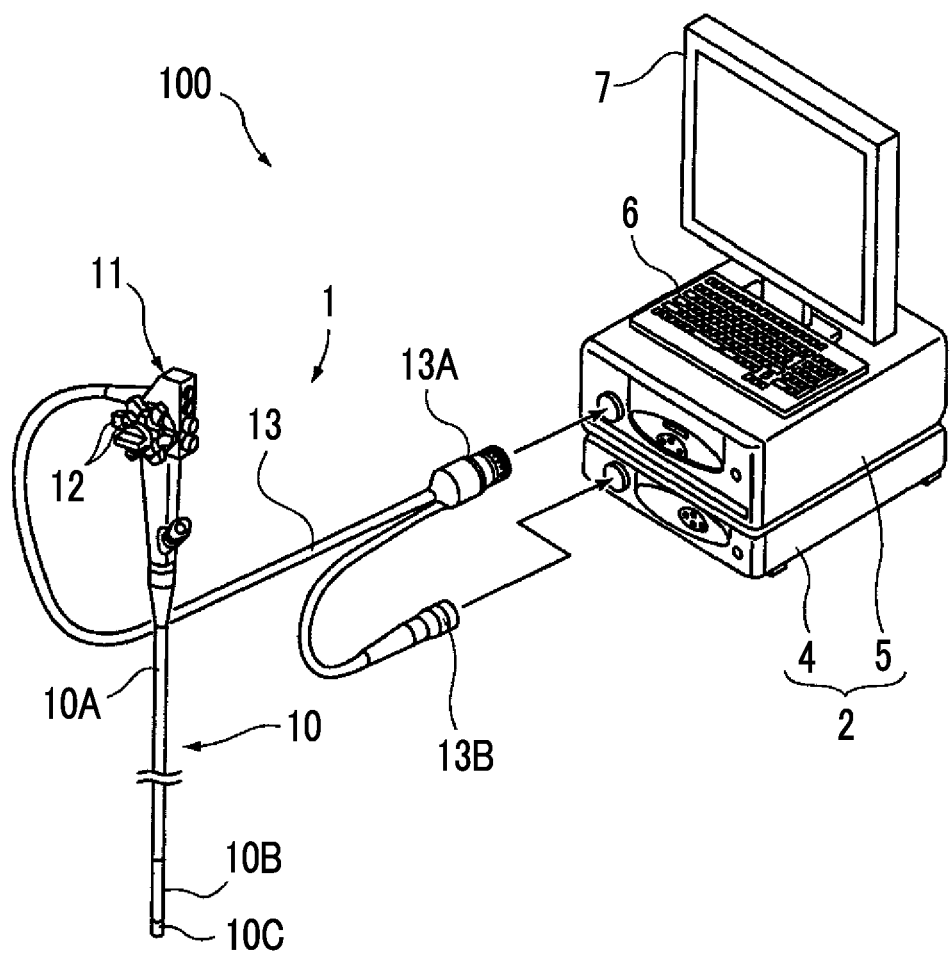
FIG. 1 is a view illustrating a schematic configuration of an endoscope device 100 that is one embodiment of the invention.

FIG. 1 is a view illustrating a schematic configuration of an endoscope device 100 that is one embodiment of the invention.

As illustrated in FIG. 1, the endoscope device 100 comprises an endoscope 1, and a body part 2 including a control device 4 and a light source device 5 to which the endoscope 1 is connected.

A display unit 7 that displays a captured image or the like, and an input unit 6 that receives an input operation are connected to the control device 4. The control device 4 controls the endoscope 1 and the light source device 5.

The endoscope 1 comprises an insertion part 10 that is a tubular member extending in one direction and is inserted into a subject, an operating part 11 that is provided at a proximal end part of the insertion part 10 and is provided with buttons for performing an observation mode switching operation, an imaging and recording operation, an air and water supply operation, a suction operation, and the like, an angle knob 12 provided adjacent to the operating part 11, and a universal cord 13 including connector parts 13A and 13B that attachably and detachably connect the endoscope 1 to the light source device 5 and the control device 4, respectively.

In addition, although illustration is omitted, various channels, such as a forceps channel for inserting treatment tools such as forceps, an air supply and water supply channel, and a suction channel, are provided inside the operating part 11 and the insertion part 10.

The insertion part 10 is constituted of a flexible part 10A that has flexibility, a bending part 10B provided at a distal end of the flexible part 10A, and a hard distal end part 10C provided at a distal end of the bending part 10B.

The bending part 10B is configured to be bendable by the turning operation of the angle knob 12. Depending on regions of the subject in which the endoscope 1 is used, the bending part 10B can be bent in an optional direction and at an optional angle and the distal end part 10C can be oriented in a desired direction.

Figure 2:
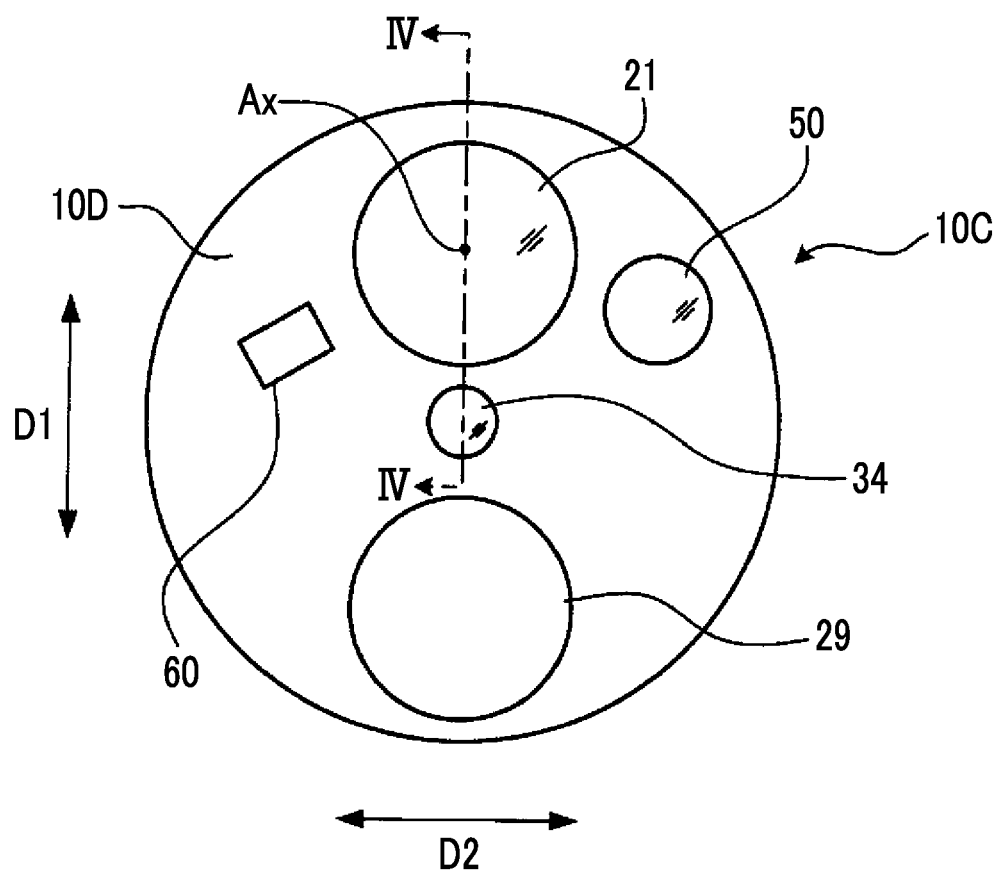
FIG. 2 is a plan view of a distal end part 10C in the endoscope device 100 illustrated in FIG. 1.

FIG. 2 is a plan view of the distal end part 10C in the endoscope device 100 illustrated in FIG. 1.

A distal end surface 10D of the distal end part 10C is substantially circular, and the distal end surface 10D is provided with an objective lens 21 among optical members that constitute the imaging optical system of the endoscope 1 located closest to the subject, an illumination lens 50, an auxiliary measurement lens 34 for emitting auxiliary measurement light to be described below, an opening 29 for allowing entrance and exit of the above-described treatment tools, and an air and water supply nozzle 60 for performing air and water supply.

An optical axis Ax of the objective lens 21 extends in a direction perpendicular to the paper surface of FIG. 2. FIG. 2 illustrates a first direction D1 that is one direction of two mutually orthogonal directions perpendicular to the optical axis Ax, and a second direction D2 that is the other direction of these two directions. In the example of FIG. 2, the objective lens 21 and the auxiliary measurement lens 34 are arranged in the first direction D1.

Figure 3:
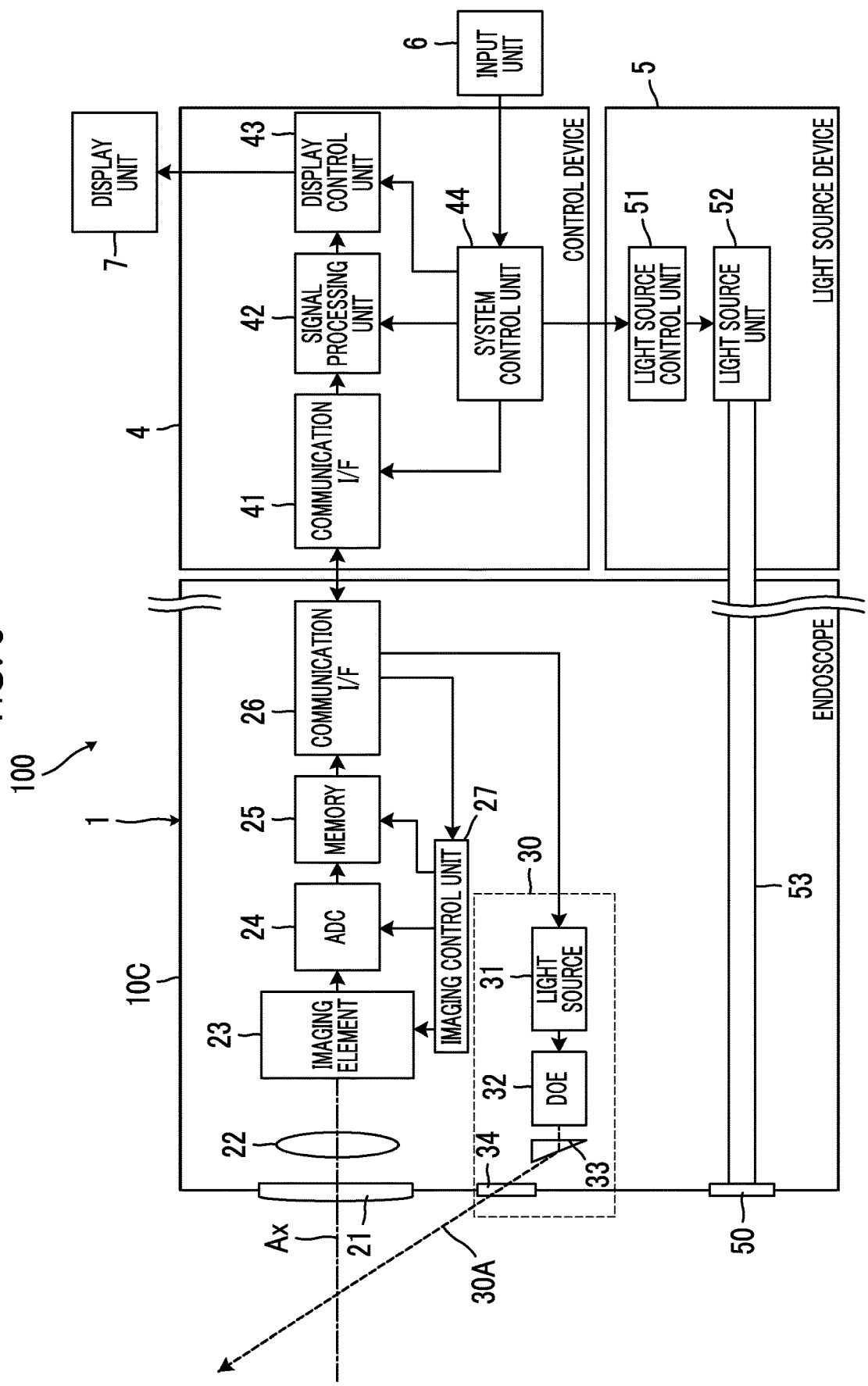
FIG. 3 is a schematic view illustrating an internal configuration of the endoscope device 100 illustrated in FIG. 1.

FIG. 3 is a schematic view illustrating an internal configuration of the endoscope device 100 illustrated in FIG. 1.

The light source device 5 comprises a light source control unit 51 and a light source unit 52.

The light source unit 52 generates illumination light for irradiating the subject. The illumination light emitted from the light source unit 52 enters a light guide 53 built in the universal cord 13, and is emitted to the subject through the illumination lens 50 provided at the distal end part 10C of the insertion part 10.

A white light source that emits white light, a plurality of light sources including the white light source and a light source (for example, a blue light source that emits blue light) that emits other color light, or the like is used as the light source unit 52. A plurality of illumination lenses 50 may be provided in conformity with the kind of light emitted from the light source unit 52 on the distal end surface 10D of the distal end part 10C.

The light source control unit 51 is connected to a system control unit 44 of the control device 4. The light source control unit 51 controls the light source unit 52 on the basis of a command from the system control unit 44.

The distal end part 10C of the endoscope 1 is provided with the imaging optical system including the objective lens 21 and a lens group 22, an imaging element 23 that images the subject through the imaging optical system, an analog/digital converter circuit (ADC) 24, a memory 25, such as a random access memory (RAM), a communication interface (I/F) 26, an imaging control unit 27, an auxiliary measurement light emitting unit 30, and the light guide 53 for guiding the illumination light emitted from the light source unit 52 to the illumination lens 50.

The light guide 53 extends from the distal end part 10C to a connector part 13A of the universal cord 13. The illumination light emitted from the light source unit 52 of the light source device 5 is allowed to enter the light guide 53 in a state where the connector part 13A of the universal cord 13 is connected to the light source device 5.

As the imaging element 23, a charge coupled device (CCD) image sensor or a complementary metal oxide semiconductor (CMOS) image sensor is used.

The imaging element 23 has a light-receiving surface on which a plurality of pixels are disposed in two dimensions, converts an optical image formed on the light-receiving surface by the above imaging optical system into an electrical signal (imaging signal) in each pixel, and outputs the converted electrical signal to the ADC 24. As the imaging element 23, for example, one in which color filters, such as an elementary color or a complementary color, is used. A set of the imaging signals output from the respective pixels of the light-receiving surface of the imaging element 23 is referred to as captured image signals.

In addition, in a case where one in which the spectrum of the white light emitted from the white light source is divided in a time-division manner by a plurality of color filters to generate the illumination light is used as the light source unit 52, one on which no color filter is mounted may be used as the imaging element 23.

The imaging element 23 may be disposed at the distal end part 10C in a state where the light-receiving surface is perpendicular to the optical axis Ax of the objective lens 21, or may be disposed at the distal end part 10C in a state where the light-receiving surface is parallel to the optical axis Ax of the objective lens 21.

The imaging optical system provided in the endoscope 1 is constituted of optical members (including the above lens group 22), such as a lens and a prism, which are present on an optical path of the light from the subject between the imaging element 23 and the objective lens 21, and the objective lens 21. There is also a case where the imaging optical system is constituted of only the objective lens 21.

The ADC 24 converts the imaging signal output from the imaging element 23 into a digital signal having a predetermined number of bits.

The memory 25 temporarily stores the imaging signal digitally converted by the ADC 24.

The communication I/F 26 is connected to a communication interface (I/F) 41 of the control device 4. The communication I/F 26 transmits the imaging signal stored in the memory 25 to the control device 4 through a signal line within the universal cord 13.

The imaging control unit 27 is connected to the system control unit 44 of the control device 4 via the communication I/F 26. The imaging control unit 27 controls the imaging element 23, the ADC 24, and the memory 25 on the basis of a command from the system control unit 44 to be received by the communication I/F 26.

The auxiliary measurement light emitting unit 30 comprises a light source 31, a diffractive optical element (DOE) 32, a prism 33, and the aforementioned auxiliary measurement lens 34.

The light source 31 emits light (specifically, visible light) of a color capable of being detected by a pixel of the imaging element 23. The light source 31 includes a light emitting element, such as a laser diode (LD) or a light emitting diode (LED), and a condensing lens that condenses the light emitted from the light emitting element.

The light emitted from the light source 31 is, for example, red light with a wavelength of 650 nm, but is not limited to having this wavelength. The light source 31 is controlled by the system control unit 44, and performs light emission on the basis of a command from the system control unit 44.

The DOE 32 converts the light emitted from the light source 31 into the auxiliary measurement light 30A that is planar light.

The prism 33 is an optical member for changing the traveling direction of the planar auxiliary measurement light 30A after being converted by the DOE 32. A plane to be formed by the planar auxiliary measurement light 30A emitted from the DOE 32 is parallel to the optical axis Ax of the objective lens 21.

The prism 33 changes the traveling direction of the planar auxiliary measurement light 30A such that this plane intersects the visual field (the visual field 21A to be described below) of the imaging optical system including the objective lens 21 and the lens group 22. The planar auxiliary measurement light 30A emitted from the prism 33 is emitted to the subject through the auxiliary measurement lens 34.

In addition, the auxiliary measurement light emitting unit 30 may emit the planar light toward the visual field of the imaging optical system from the distal end part 10C, and is not limited to having a configuration illustrated in FIG. 3.

For example, a configuration in which the light source 31 is provided in the light source device 5 and the light emitted from the light source 31 is guided to the DOE 32 by an optical fiber may be adopted.

Additionally, a configuration in which the planar auxiliary measurement light 30A is emitted in a direction crossing the visual field of the imaging optical system by inclining the orientation of the light source 31 and the DOE 32 with respect to the optical axis Ax without using the prism 33 may be adopted.

The control device 4 comprises the communication I/F 41 connected to the communication I/F 26 of the endoscope 1 by the universal cord 13, a signal processing unit 42, a display control unit 43, and the system control unit 44.

The communication I/F 41 receives the imaging signal transmitted from the communication I/F 26 of the endoscope 1 and transmits the imaging signal to the signal processing unit 42.

The signal processing unit 42 has a memory for temporarily storing the imaging signal received from the communication I/F 41 built therein, and processes captured image signals, which are a set of the imaging signals stored in the memory, to generate a captured image.

The display control unit 43 causes the display unit 7 to display the captured image generated by the signal processing unit 42.

The system control unit 44 controls the respective units of the control device 4, and sends commands to the imaging control unit 27 of the endoscope 1, the light source control unit 51 of the light source device 5, and the light source 31, and integrally controls the entire endoscope device 100.

The system control unit 44 performs the control of the imaging element 23 via the imaging control unit 27. Additionally, the system control unit 44 performs the control of the light source unit 52 via the light source control unit 51. Additionally, the system control unit 44 performs the control of the light source 31.

Each of the imaging control unit 27, the light source control unit 51, the signal processing unit 42, the display control unit 43, and the system control unit 44 includes various processors that execute a program to perform processing, a random access memory (RAM), and a read only memory (ROM).

The various processors include a central processing unit (CPU) that is a general-purpose processor that executes a program to perform various kinds of processing, a programmable logic device (PLD), which is a processor capable of changing a circuit configuration after manufacture, such as a field programmable gate array (FPGA), or an exclusive electric circuit, which is a processor having a circuit configuration exclusively designed to execute specific processing, such as an application specific integrated circuit (ASIC).

The structure of these various processors is, more specifically, an electric circuit in which circuit elements, such as semiconductor elements, are combined together.

Each of the imaging control unit 27, the light source control unit 51, the signal processing unit 42, the display control unit 43, and the system control unit 44 may be constituted of one of the various processors, or may be constituted of a combination (for example, a combination of a plurality of FPGAs or a combination of a CPU and an FPGA) of two or more processors of the same type or different types.

Figure 4:
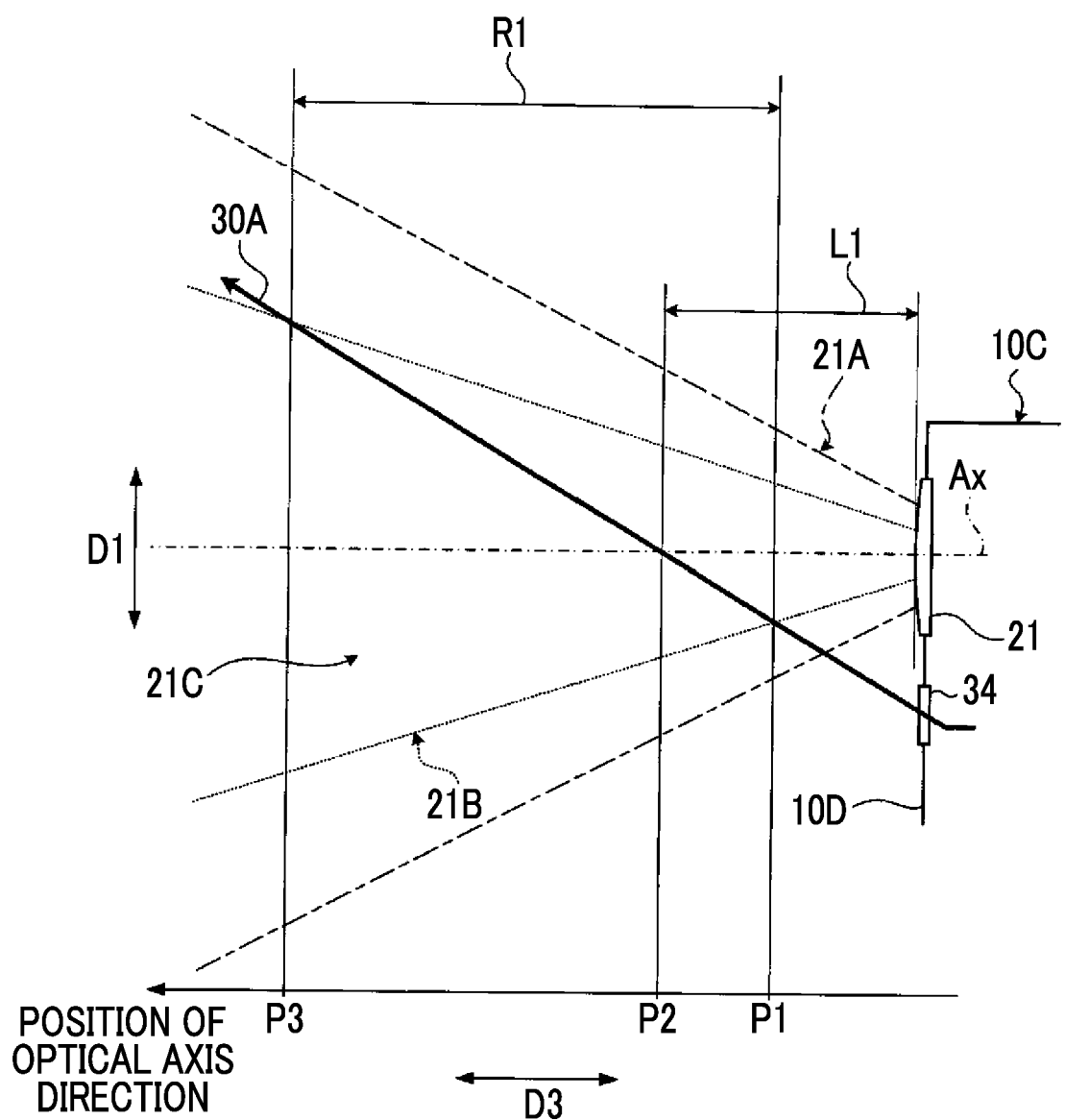
FIG. 4 is a cross-sectional schematic view taken along line IV-IV (a line that passes through an optical axis Ax of an objective lens 21 and extends in a first direction D1) at the distal end part 10C illustrated in FIG. 2.

FIG. 4 is a cross-sectional schematic view taken along line IV-IV (a line that passes through the optical axis Ax of the objective lens 21 and extends in the first direction D1) in the distal end part 10C illustrated in FIG. 2. In FIG. 4, illustration of those other than the objective lens 21 and the auxiliary measurement lens 34 as components of the distal end part 10C is omitted. In FIG. 4, an optical axis direction D3 that is a direction parallel to the optical axis Ax of the objective lens 21 is illustrated.

The imaging optical system including the objective lens 21 has the visual field 21A illustrated by one-dot chain line in FIG. 4. In the imaging element 23, it is possible to image the subject present within the visual field 21A. The visual field 21A has a circular shape in a cross-section perpendicular to the optical axis Ax.

A depth of field, which is a range in which the subject is in focus, is present in the imaging optical system including the objective lens 21. The depth of field R1 of the imaging optical system illustrated in FIG. 4 is a range between a position P1 and a position P3 in the optical axis direction D3.

Although this depth of field R1 is optionally determined, in the endoscope, the design of the imaging optical system is often performed such that the range of 3 mm or more and 100 mm or less from the objective lens 21 is the depth of field R1.

That is, the position P1 is a position where the distance from the distal end part (a point at a distal end closest to the subject in a direction along the optical axis Ax of the objective lens 21) of the objective lens 21 is 3 mm, and the position P3 is a position where the distance from the distal end part of the objective lens 21 is 100 mm. In addition, these numerical values are examples, and the invention is not limited to the numerical values.

Hence, in the imaging element 23, regarding the subject present within the visual field 21A and within the depth of field R1, it is possible to image this subject with high resolution.

In addition, in a case where the visual field 21A is expressed by an angle of view, the visual field is a range of, for example, 140° to 170°. In this way, in the endoscope 1, the visual field 21A is set wide. For this reason, in the optical image of the subject formed on the light-receiving surface of the imaging element 23 by the imaging optical system, distortion occurs around the visual field 21A.

In the endoscope device 100, an effective visual field 21B illustrated by a broken line in FIG. 4 is determined in advance as a range where distortion of the optical image does not occur substantially in the visual field 21A. The effective visual field 21B is a range suitable for displaying scales serving as indexes of the size of subjects to be described below. Hereinafter, an overlapping range between the effective visual field 21B and the depth of field R1 is referred to as the effective imaging range 21C.

A subject included in the effective imaging range 21C among subjects included in a captured image obtained by being imaged by the imaging element 23 is capable of being observed with high resolution and with no distortion.

The auxiliary measurement light emitting unit 30 emits the auxiliary measurement light 30A in a state where the plane formed by the auxiliary measurement light 30A intersects the optical axis Ax at the position P2 in the optical axis direction D3. The position P2 is within the depth of field R1, and the distance L1 from the distal end part of the objective lens 21 to the position P2 is 5 mm or more and 20 mm or less.

A range of 5 mm or more and 20 mm or less (hereinafter referred to as an optimal observation range) from the distal end part of the objective lens 21 in the optical axis direction D3 is, particularly, a range where the observation frequency of the subject is high in endoscopy.

In a case where there is the object to be observed, such as a polyp, there are many cases where a doctor who uses the endoscope 1 operates the endoscope 1 such that the object to be observed falls within the optimal observation range, and checks the object to be observed, which is present in the optimal observation range, on the captured image.

In a case where the object to be observed is present closer to a near side than the optimal observation range, there is a case where the object to be observed becomes excessively large in the captured image and is not suitable for diagnosis. On the other hand, in a case where the object to be observed is present closer to a far side than the optimal observation range, there is a case where the detailed state of the object to be observed is not easily observed and is not be suitable for diagnosis. From these circumstances, the frequency at which the object to be observed is observed in a state where the object to be observed is present in the optimal observation range is high.

In addition, there is also a case where a lower limit value of the optimal observation range is 3 mm, which is almost the limit of the depth of field R1 depending on doctors. For this reason, the distance L1 may be in a range of 3 mm or more and 20 mm or less.

The auxiliary measurement light emitting unit 30 emits the auxiliary measurement light 30A in a case where the plane formed by the auxiliary measurement light 30A passes through an end part on one side (a lower side in the example of FIG. 4) in the first direction D1 at the end part of the effective imaging range 21C on the objective lens 21 side and passes through the end part on the other side (an upper side in the example of FIG. 4) in the first direction D1 at an end part of the effective imaging range 21C on a side opposite to the objective lens 21 side.

Figure 5:
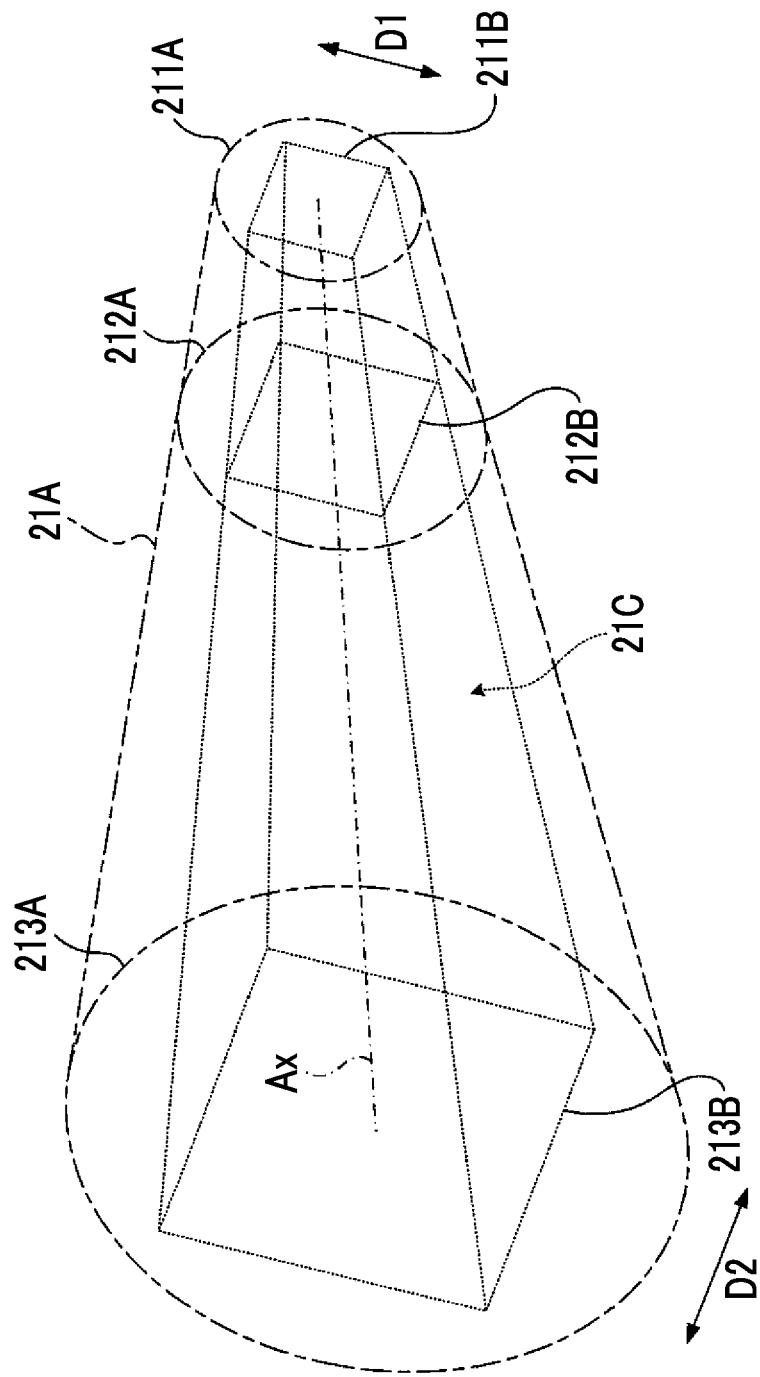
FIG. 5 is a perspective view illustrating a visual field 21A and an effective imaging range 21C within a depth of field R1 illustrated in FIG. 4.
Figure 6:
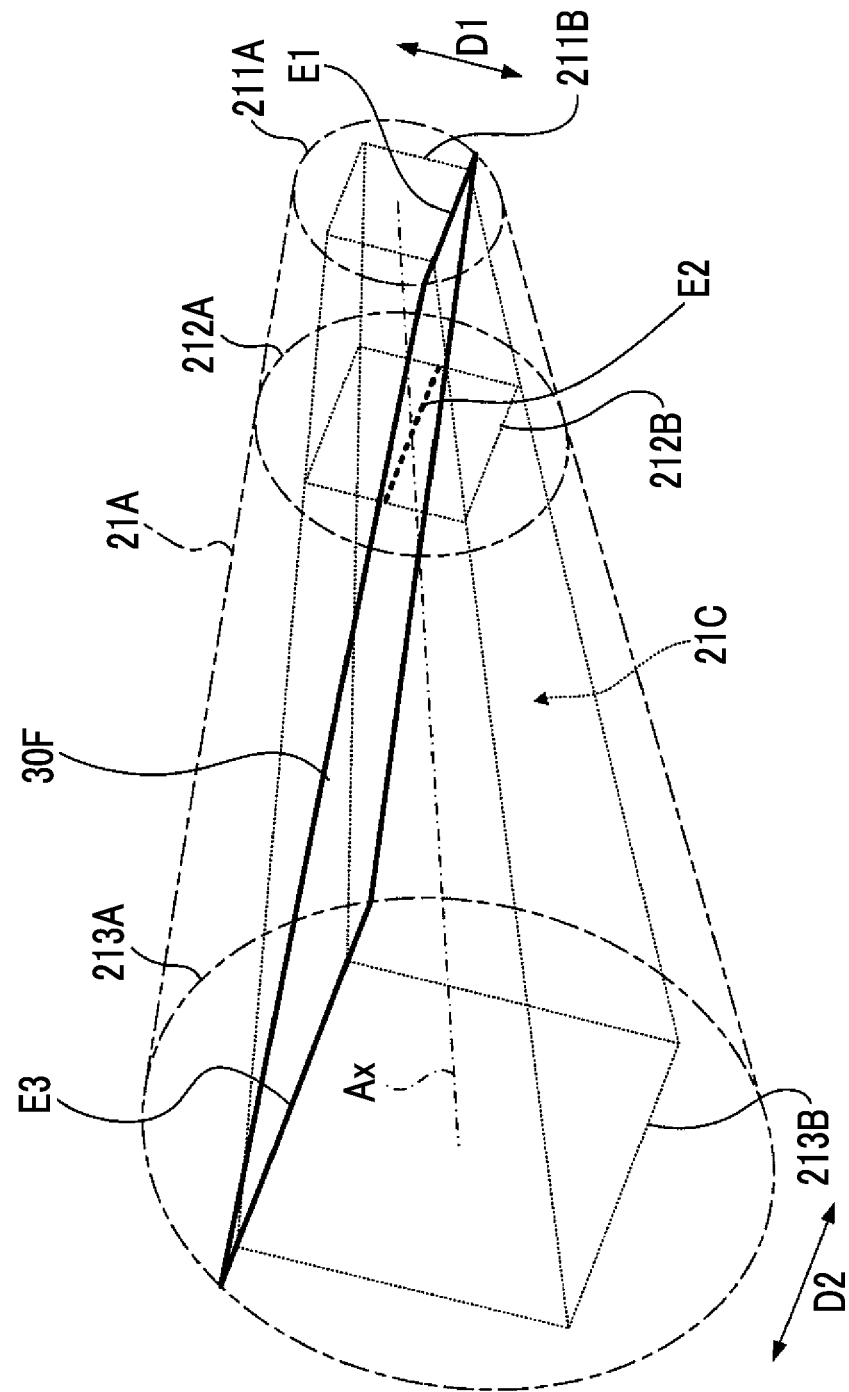
FIG. 6 is a perspective view illustrating a relationship between the visual field 21A and the effective imaging range 21C that are illustrated in FIG. 5, and a plane 30F formed by auxiliary measurement light 30A.

FIG. 5 is a perspective view illustrating the visual field 21A and the effective imaging range 21C within the depth of field R1 illustrated in FIG. 4. FIG. 6 is a perspective view illustrating a relationship between the visual field 21A and the effective imaging range 21C that are illustrated in FIG. 5, and the plane 30F formed by the auxiliary measurement light 30A.

In FIGS. 5 and 6, an end part 211A on the objective lens 21 side and an end part 213A on the side opposite to the objective lens 21 side are illustrated as end parts of the visual field 21A in the optical axis direction D3 within the depth of field R1. Additionally, a cross-section 212A in a plane perpendicular to the optical axis Ax at the position P2 of the visual field 21A within the depth of field R1 is illustrated in FIGS. 5 and 6.

Additionally, in FIGS. 5 and 6, an end part 211B on the objective lens 21 side and an end part 213B on the side opposite to on the objective lens 21 side are illustrated as end parts of the effective imaging range 21C in the optical axis direction D3. Additionally, a cross-section 212B in the plane perpendicular to the optical axis Ax at the position P2 of the effective imaging range 21C is illustrated in FIGS. 5 and 6.

As illustrated in FIG. 5, the shape of the effective imaging range 21C in a cross-section perpendicular to the optical axis Ax is a square shape in which the optical axis Ax passes through the center. The square shape is constituted of two sides parallel to the first direction D1 and two sides parallel to the second direction D2.

As illustrated in FIG. 6, the plane 30F formed by the auxiliary measurement light 30A intersects the visual field 21A in a state which the plane passes through an end part E1 on one side (a radially inner side of the distal end surface 10D) in the first direction D1 at the end part 211B of the effective imaging range 21C, passes through a centerline E2 in the first direction D1 in the cross-section 212B of the effective imaging range 21C, and passes through an end part E3 on the other side (a radially outer side of the distal end surface 10D) in the first direction D1 at the end part 213B of the effective imaging range 21C.

Figure 7:
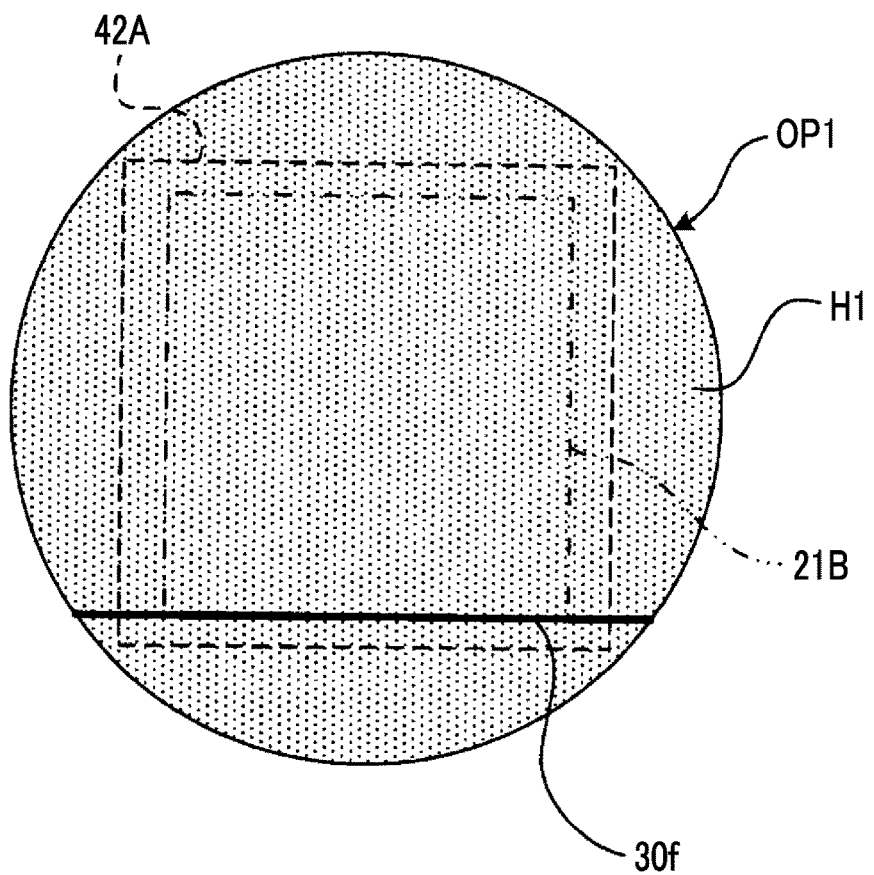
FIG. 7 is a view illustrating an example of an optical image formed by an imaging optical system of the endoscope device 100 illustrated in FIG. 1.

By virtue of such a configuration, for example, a planar subject H1 (a subject in which the distance from the distal end part of the objective lens 21 is uniform as a whole) perpendicular to the optical axis Ax is disposed at the position P1 of FIG. 4, and an optical image OP1 obtained by forming an image of the subject H1 by the imaging optical system is illustrated in FIG. 7. The effective visual field 21B is auxiliarily illustrated in FIG. 7.

The optical image OP1 illustrated in FIG. 7 includes the subject H1, and an intersection line 30f between the subject H1 and the plane 30F that is formed by the auxiliary measurement light 30A being emitted to the subject H1.

Figure 8:
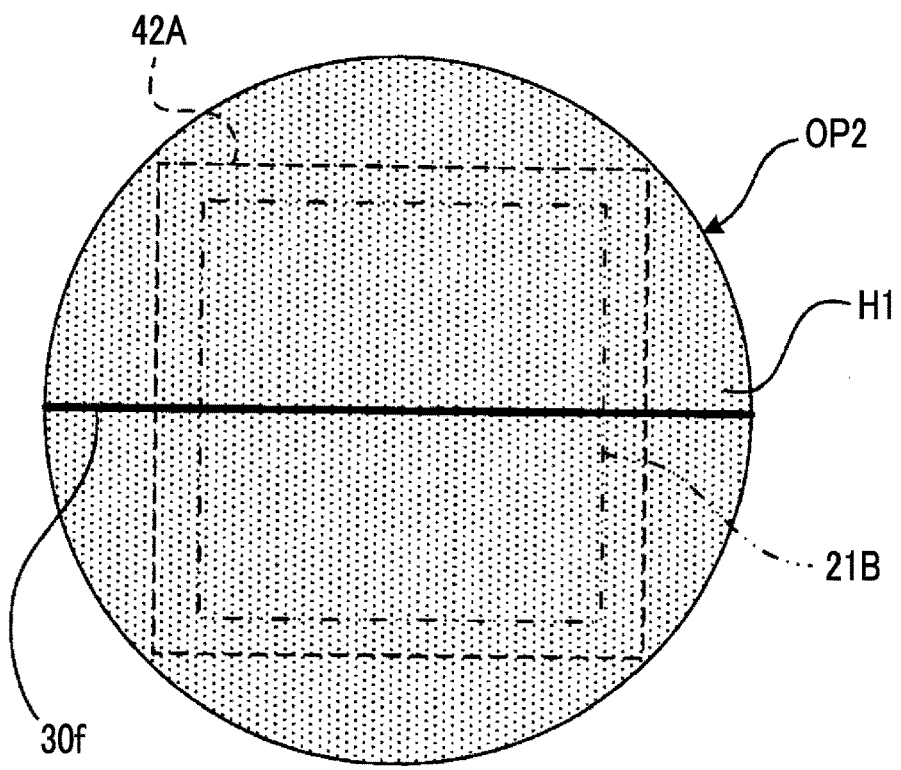
FIG. 8 is a view illustrating an example of an optical image formed by the imaging optical system of the endoscope device 100 illustrated in FIG. 1.

Additionally, the subject H1 is disposed at the position P2 of FIG. 4, and an optical image OP2 obtained by forming an image of the subject H1 by the imaging optical system is as illustrated in FIG. 8. The effective visual field 21B is auxiliarily illustrated in FIG. 8.

The optical image OP2 illustrated in FIG. 8 includes the subject H1, and the intersection line 30f between the subject H1 and the plane 30F that is formed by the auxiliary measurement light 30A being emitted to the subject H1.

Figure 9:
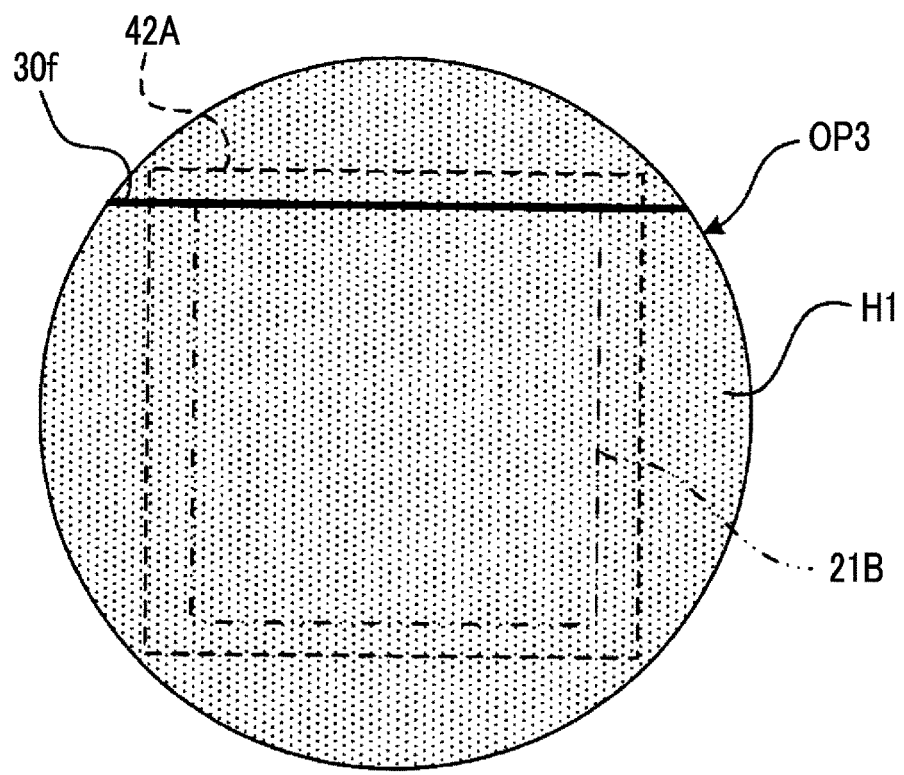
FIG. 9 is a view illustrating an example of an optical image formed by the imaging optical system of the endoscope device 100 illustrated in FIG. 1.

Additionally, the subject H1 is disposed at the position P3 of FIG. 4, and an optical image OP3 obtained by forming an image of the subject H1 by the imaging optical system is as illustrated in FIG. 9. The effective visual field 21B is auxiliarily illustrated in FIG. 9.

The optical image OP3 illustrated in FIG. 9 includes the subject H1, and the intersection line 30f between the subject H1 and the plane 30F that is formed by the auxiliary measurement light 30A being emitted to the subject H1.

In this way, the position of the intersection line 30f in an optical image to be formed on the light-receiving surface of the imaging element 23 is moved in one direction depending on the distance of the subject from the distal end part of the objective lens 21.

The signal processing unit 42 of the control device 4 processes captured image signals converted into electrical signals from the optical images as illustrated in FIGS. 7 to 9 to generate captured images. In the present embodiment, the signal processing unit 42 generates captured images corresponding to optical images within a predetermined signal processing range 42A illustrated in FIGS. 7 to 9. Of course, the signal processing unit 42 may generate a captured image corresponding to the entire optical image.

The display control unit 43 of the control device 4, as illustrated in FIGS. 7 to 9, sets a direction in which the intersection line 30f included in a captured image obtained in a case where the subject H1 of which the distance from the distal end part of the objective lens 21 is uniform is imaged extend, as a horizontal direction of the captured image generated by the signal processing unit 42, and causes the display unit 7 to display the captured image in accordance with this setting.

That is, the display control unit 43 causes the display unit 7 to display the captured image such that the horizontal direction of the captured image coincides with the horizontal direction on a display surface of the display unit 7.

Hence, the intersection line 30f in the captured image displayed on the display unit 7 changes in the position thereof in a vertical direction as the distance to the subject on which the intersection line 30f is formed changes.

In the following, description will be made assuming that the intersection line 30f displayed on the display unit 7 moves toward the top from the bottom in the vertical direction on a display screen as the subject moves away from the objective lens 21.

The display control unit 43 causes the display unit 7 to display a scale indicating the actual size of the intersection line 30f so as to overlap the intersection line 30f in a case where the display unit 7 is made to display a captured image including the intersection line 30f The scales constitute a scale serving as an index of a size of subjects.

A data table showing a relationship between positions in the vertical direction in the captured image generated by the signal processing unit 42 and actual sizes of the image per pixel at the positions is stored in the ROM built in the display control unit 43.

For example, graph paper on which, for example, 1 mm squares are lined up is prepared as the above-described subject H1, and the graph paper is imaged by the imaging element 23, in a state where this graph paper is put at an optional distance from the distal end part of the objective lens 21.

Then, a position yn of the intersection line 30f in the vertical direction in the captured image is found. Additionally, the length of the intersection line 30f included in the captured image obtained by this imaging is measured using the squares of the graph paper. An actual size per pixel at the above position yn is found by dividing the measured length of the intersection line 30f by the total number of pixels of the captured image in the horizontal direction. Finally, information on the actual size per pixel and the position yn are associated with each other and are stored in the ROM.

By repeatedly such operations performing while finely changing the position of the graph paper in the optical axis direction D3, the above-described data table is created.

Specifically, the display control unit 43 detects the intersection line 30f from the captured image generated by the signal processing unit 42, and sets one of a large number of pixel data items constituting the intersection line 30f as a starting point.

Then, the display control unit 43 sequentially selects the large number of pixel data items in the horizontal direction from this starting point. From the position of a selected pixel data item in the vertical direction and the above data table, the display control unit 43 obtains information on an actual size per pixel at the position.

The display control unit 43 integrates the actual size obtained in this way whenever pixel data items are selected, and specifies a pixel data item selected in a case where the integrated value becomes an integral multiple of unit length (for example, 1 mm), as a pixel data item on which a scale is to overlap. Additionally, the display control unit 43 also specifies the pixel data item of the starting point as a pixel data item on which a scale is overlap.

The display control unit 43 causes scales (for example, a vertical line that extends in the vertical direction) indicating intervals of the unit length to be displayed on the pixel data item specified by such processing. Accordingly, the scales serving as the indexes of the size of subjects are displayed on the display unit 7.

In addition, the scale display method is an example and is not limited to this.

Figure 10:
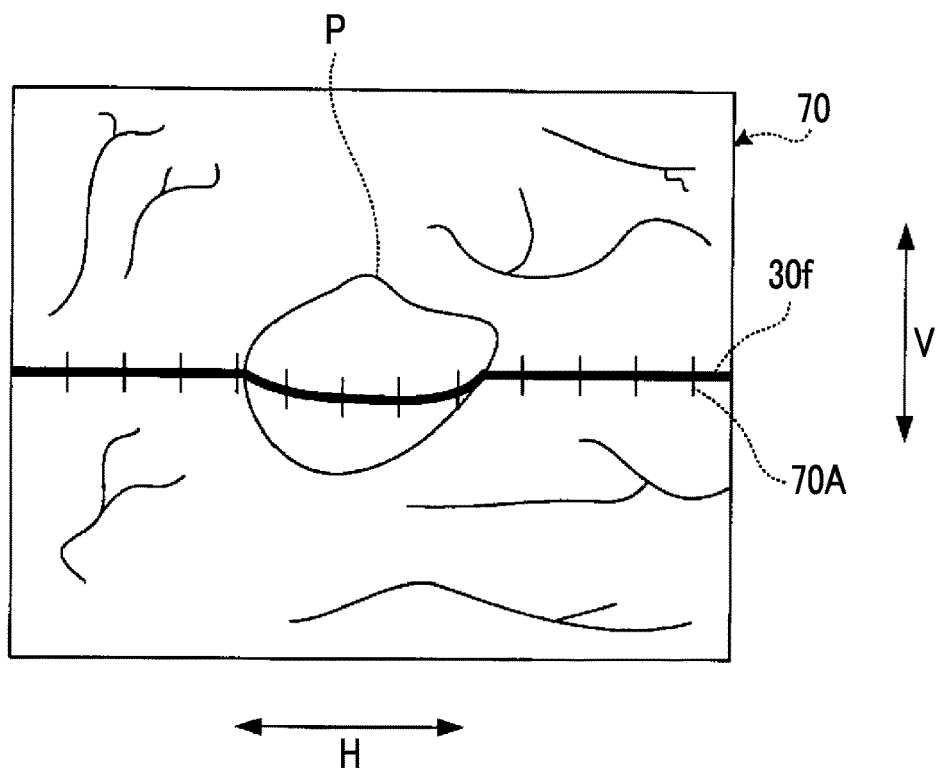
FIG. 10 is a view illustrating an example of a captured image displayed on a display unit 7 of the endoscope device 100 in a state where a polyp P is at the position of a distance L1 from the objective lens 21.

FIG. 10 is a view illustrating an example of a captured image displayed on the display unit 7 of the endoscope device 100 in a state where a polyp P is at the position of the distance L1 from the distal end part of the objective lens 21.

Figure 11:
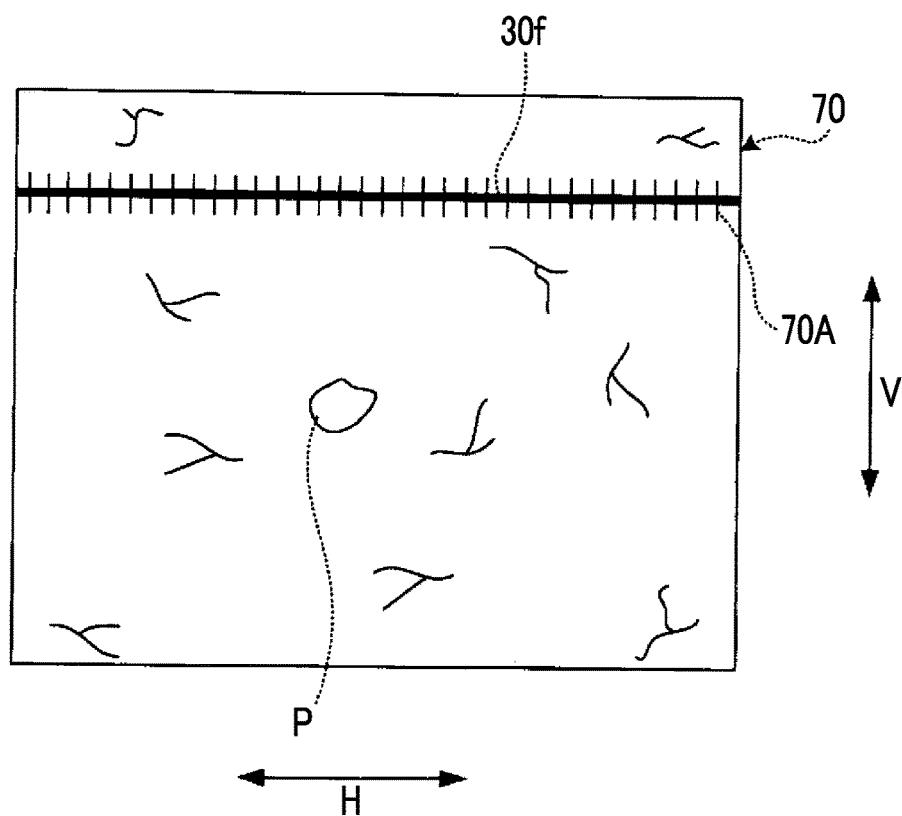
FIG. 11 is a view illustrating an example of the captured image in a state where the polyp P is at a position farther from the objective lens 21 than that in the state illustrated in FIG. 10.

FIG. 11 is a view illustrating an example of the captured image in a state where the polyp P is at a position farther from the objective lens 21 than that in the state illustrated in FIG. 10.

Figure 12:
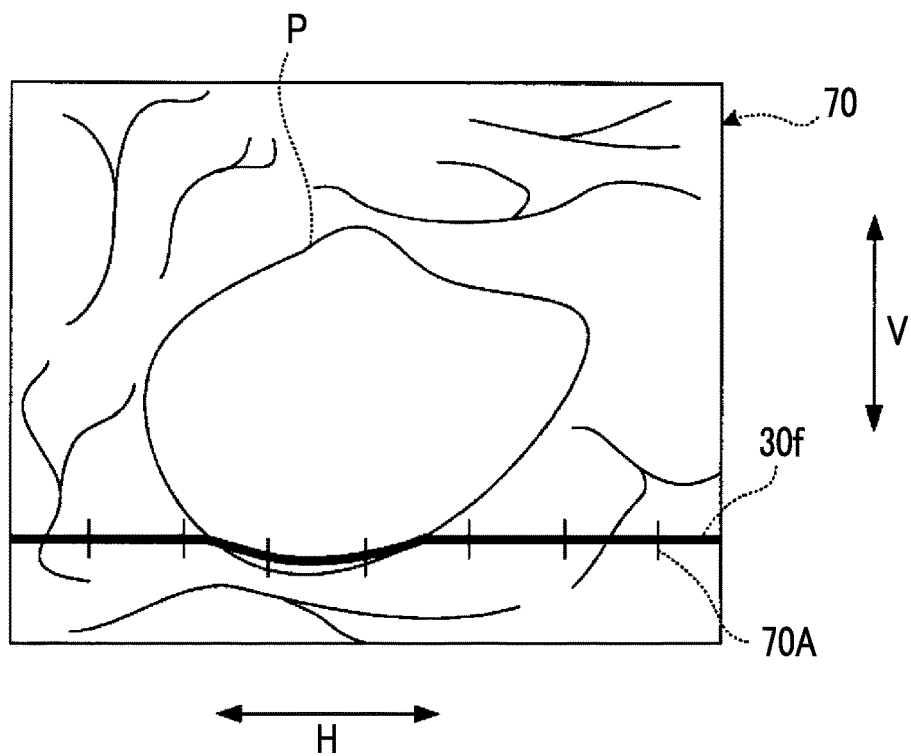
FIG. 12 is a view illustrating an example of the captured image in a state where the polyp P is at a position closer to the objective lens 21 than that in the state illustrated in FIG. 10.

FIG. 12 is a view illustrating an example of the captured image in a state where the polyp P is at a position closer to the objective lens 21 than that in the state illustrated in FIG. 10.

A direction H illustrated in FIGS. 10 to 12 indicates a horizontal direction of the display screen of the display unit 7. A direction V illustrated in FIGS. 10 to 12 indicates a vertical direction of the display screen of the display unit 7.

As illustrated in FIGS. 10 to 12, a captured image 70 displayed on the display unit 7 includes the intersection line 30f, and scales 70A indicating the unit length. As illustrated in FIGS. 10 to 12, as the intersection line 30f is closer to an upper side in the direction V on the display screen, the intervals of the scales 70A are finely displayed.

As described above, in the endoscope device 100, the position P2 of an intersection point between the plane 30F formed by the auxiliary measurement light 30A and the optical axis Ax of the objective lens 21 is present within an optimal observation range of 5 mm or more and 20 mm or less from the distal end part of the objective lens 21.

For this reason, the user can cause the object to be observed and the intersection line 30f to be displayed near the center of the display screen as illustrated in FIG. 10 simply by operating the endoscope 1 such that the object to be observed, such as a polyp, falls within the optimal observation range, and performing the operations that are generally performed, such as operating the endoscope 1 such that the object to be observed is near the center of the captured image displayed on the display unit 7.

In the state that illustrates in FIG. 10, since the polyp P is in the optimal observation range, the user can check the state of the polyp P in detail. Additionally, the intersection line 30f included in the captured image 70 is displayed on the polyp P in a portion that has almost no distortion on the captured image 70. For this reason, in a case where measuring the size of the polyp P using the intersection line 30f, the measurement can be performed with high accuracy.

In this way, according to the endoscope device 100, simply by performing familiar operations, such as performing the operation of the endoscope 1 such that the object to be observed is within the optimal observation range and near the center of the captured image, the user can accurately know the state of the object to be observed and the size of the object to be observed, and can make the endoscope device useful for diagnosis or the like.

Additionally, according to the endoscope device 100, the position P2 of the intersection point between the plane 30F formed by the auxiliary measurement light 30A and the optical axis Ax of the objective lens 21 is fixed. For this reason, an increase in the manufacturing cost of the endoscope device 100 can be prevented as compared to a configuration in which the auxiliary measurement light 30A is swept.

Additionally, according to the endoscope device 100, by operating the endoscope 1 such that the intersection line 30f displayed on the display unit 7 is near the center of the captured image, it is also possible to put the object to be observed within the optimal observation range. For this reason, the state of the object to be observed can be accurately and quickly checked.

Additionally, as illustrated in FIG. 6, the endoscope device 100 has a configuration in which the plane 30F passes through the end part E1, and passes through the end part E3, and crosses the effective imaging range 21C. For this reason, in a case where the object to be observed is present in the effective imaging range 21C, the plane 30F necessarily intersects the object to be observed. Therefore, the size of the object to be observed can be measured. Hence, even in a situation where the object to be observed cannot be put into the optimal observation range, the size of the object to be observed can be measured, and the endoscope device can be used for diagnosis.

Additionally, in the endoscope device 100, the scales indicating the actual size of the intersection line 30f are displayed on the intersection line 30f included in the captured image displayed on the display unit 7. For this reason, the user can ascertain the size of the object to be observed simply by visual observation according to the scales.

Since the user can know the size of the object to be observed without performing a special operation of selecting two points on the captured image, the user can proceed endoscopy smoothly.

In addition, the display control unit 43 may not cause the scales 70A illustrated in FIGS. 10 to 12 to be always displayed, but cause the scales to be displayed only in a case where the operation of a button provided in the operating part 11 is made and there is an instruction from the user. According to this configuration, the scales 70A can be displayed only in a case where the user wants to perform measurement, and the observation visual field can be extended in a case where no measurement is performed.

Hereinafter, a modification example of the endoscope device 100 will be described.

FIRST MODIFICATION EXAMPLE

It is preferable that the display control unit 43 adds the information indicating the effective visual field 21B to the captured image generated by the signal processing unit 42 and causes the display unit 7 to display the captured image to which this information is added.

Figure 13:
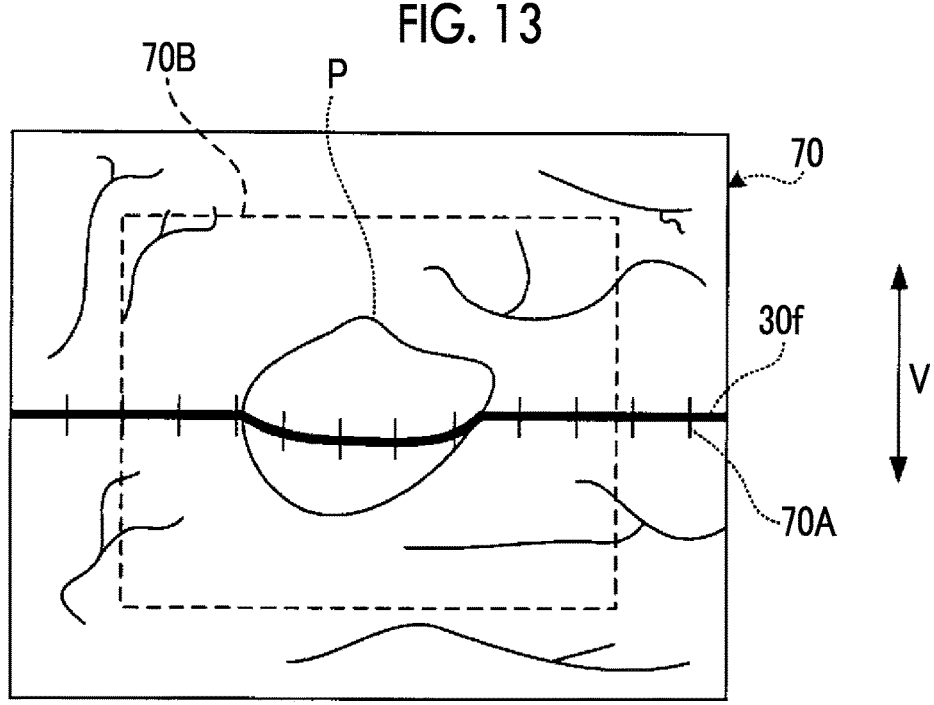
FIG. 13 is a view illustrating an example of the captured image displayed on the display unit 7 of the endoscope device 100 of a first modification example.

FIG. 13 is a view illustrating an example of the captured image displayed on the display unit 7 of the endoscope device 100 of a first modification example.

The captured image 70 illustrated in FIG. 13 is the same as that illustrated in FIG. 10 except that a frame 70B equivalent to the effective visual field 21B is added.

In this way, as the frame 70B indicating the effective visual field 21B is displayed on the captured image, the user can ascertain which range on the captured image is imaged without distortion. For this reason, since the scales 70A present outside the frame 70B are influenced by the distortion, a determination that the scales are not utilized for measurement is allowed, and generation of a measurement error can be prevented.

SECOND MODIFICATION EXAMPLE

It is preferable that, in a case where the entire intersection line 30f overlaps a portion outside the effective visual field 21B in the captured image generated by the signal processing unit 42, the display control unit 43 causes the scales 70A on the intersection line 30f not to be displayed.

Figure 14:
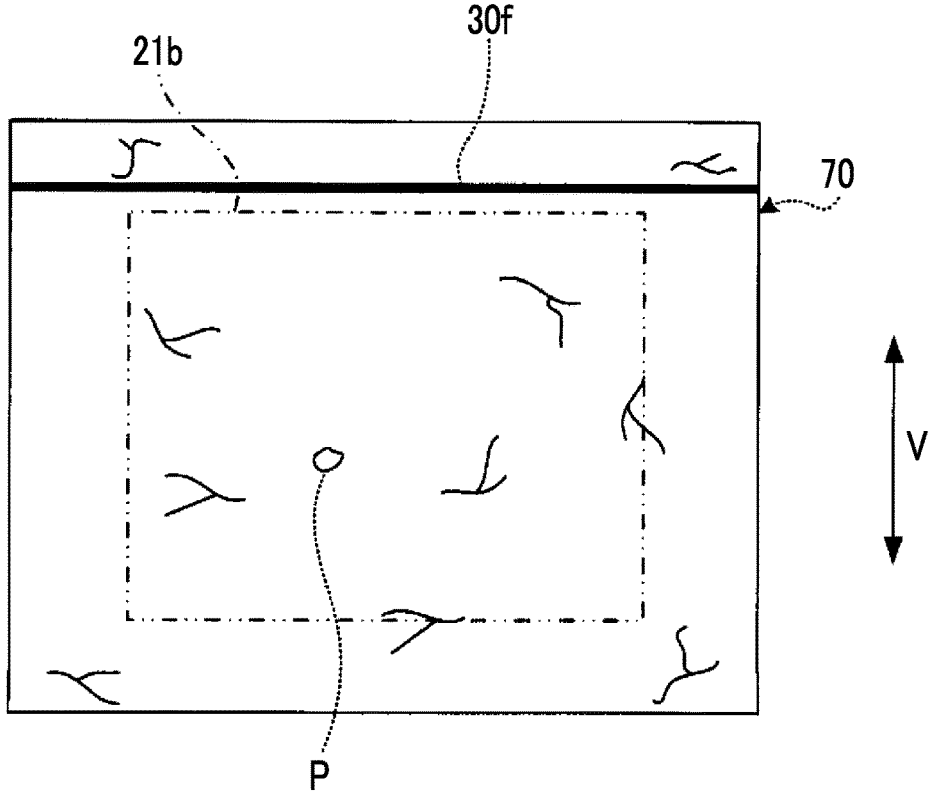
FIG. 14 is a view illustrating an example of the captured image displayed on the display unit 7 of the endoscope device 100 of a second modification example.

FIG. 14 is a view illustrating an example of the captured image displayed on the display unit 7 of the endoscope device 100 of a second modification example.

In the captured image 70 illustrated in FIG. 14, the entire intersection line 30f is located outside a range 21b equivalent to the effective visual field 21B. In addition, the range 21b is not displayed on the display unit 7 and is illustrated only for description.

In this state, the display control unit 43 does not cause the scales to be displayed on the intersection line 30f. On the other hand, the display control unit 43 causes the scales to be displayed on the intersection line 30f in a case where the intersection line 30f overlaps the range 21b.

According to this configuration, measurement can be prevented from being performed by the intersection line 30f in a large distortion range, and a measurement error can be prevented.

THIRD MODIFICATION EXAMPLE

It is preferable that, in a case where the entire intersection line 30f overlaps the portion outside the effective visual field 21B in the captured image generated by the signal processing unit 42, the display control unit 43 changes the display form of the scales on the intersection line 30f for the case where the entire intersection line 30f overlaps the portion of the effective visual field 21B.

Figure 15:
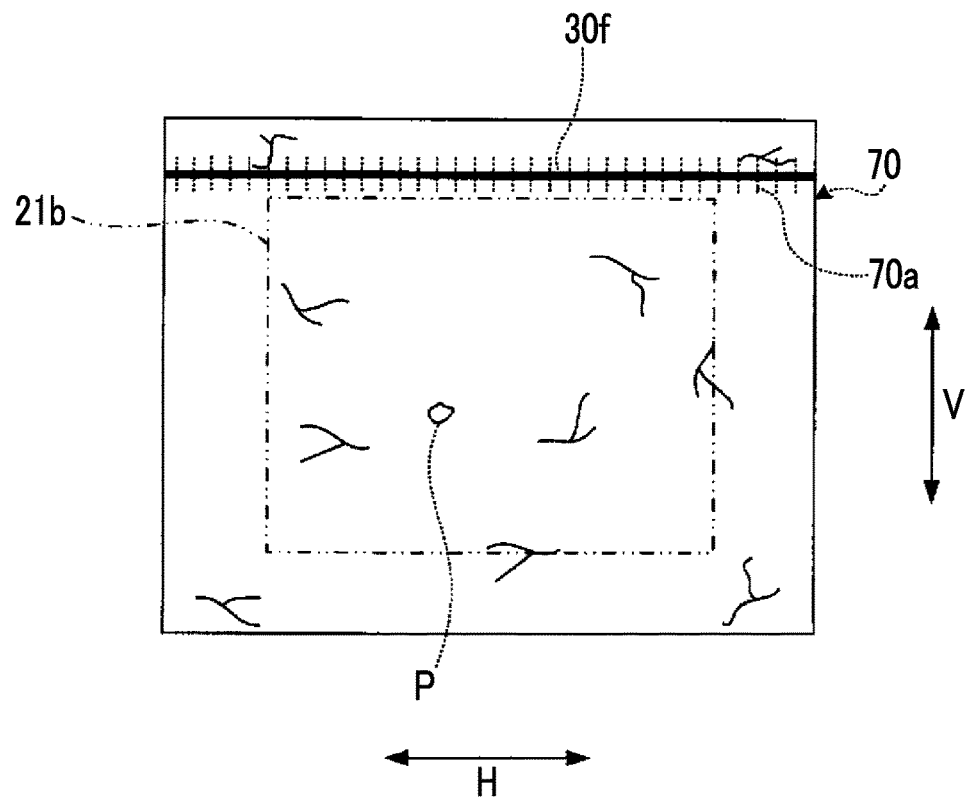
FIG. 15 is a view illustrating an example of the captured image displayed on the display unit 7 of the endoscope device 100 of a third modification example.

FIG. 15 is a view illustrating an example of the captured image displayed on the display unit 7 of the endoscope device 100 of a third modification example.

In the captured image 70 illustrated in FIG. 15, the entire intersection line 30f is located outside the range 21b equivalent to the effective visual field 21B. In addition, the range 21b is not displayed on the display unit 7 and is illustrated only for description.

In this state, the display control unit 43 displays scales 70a of a display form different from the scales 70A illustrated to FIG. 13 on the intersection line 30f.

The scales 70a are displayed, for example, in a color different from that of the scales 70A, or are displayed in a line type (for example, a broken line) different from the scales 70A.

According to this configuration, the user can recognize that the intersection line 30f is outside the effective visual field 21B depending on the difference in the display form of the scales. For this reason, measurement can be prevented from being performed by the intersection line 30f in a large distortion range, and a measurement error can be prevented.

FOURTH MODIFICATION EXAMPLE

It is preferable that, in a case where the intersection line 30f overlaps the effective visual field 21B and the portion outside the effective visual field 21B in the captured image generated by the signal processing unit 42, the display control unit 43 causes the scales 70A on the intersection line 30f overlapping the portion outside the effective visual field 21B not to be displayed.

Figure 16:
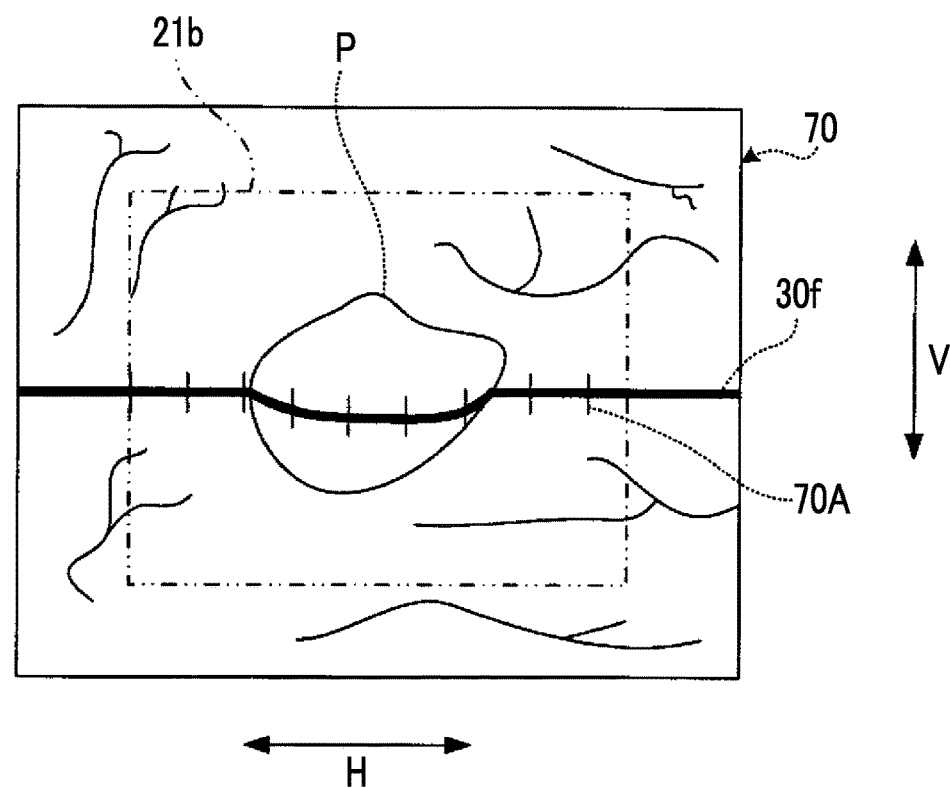
FIG. 16 is a view illustrating an example of the captured image displayed on the display unit 7 of the endoscope device 100 of a fourth modification example.

FIG. 16 is a view illustrating an example of the captured image displayed on the display unit 7 of the endoscope device 100 of a fourth modification example.

The captured image 70 illustrated in FIG. 16 is the same as one illustrated in FIG. 10 except that the scales 70A on the intersection line 30f is not displayed outside the range 21b equivalent to the effective visual field 21B. In addition, the range 21b is not displayed on the display unit 7 and is illustrated only for description.

In this way, as the scales 70A are displayed only on the portion of the intersection line 30f overlapping the effective visual field 21B, measurement can be prevented from being performed by the intersection line 30*f* in a large distortion range, and a measurement error can be prevented.

FIFTH MODIFICATION EXAMPLE

It is preferable that in a case where the intersection line 30*f* overlaps the effective visual field 21B and the portion outside the effective visual field 21B in the captured image generated by the signal processing unit 42, the display control unit 43 changes the display form of the scales 70A on the intersection line 30*f* overlapping the portion outside the effective visual field 21B with respect to the scales 70A on the intersection line 30*f* overlapping the effective visual field 21B.

Figure 17:
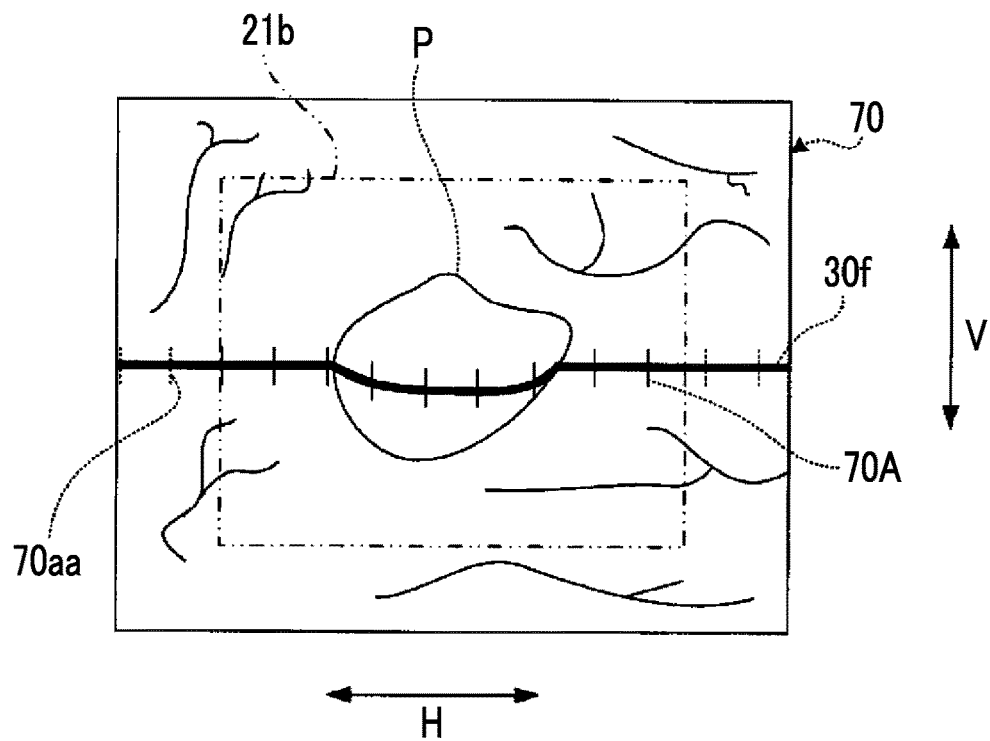
FIG. 17 is a view illustrating an example of the captured image displayed on the display unit 7 of the endoscope device 100 of a fifth modification example.

FIG. 17 is a view illustrating an example of the captured image displayed on the display unit 7 of the endoscope device 100 of a fifth modification example.

In the captured image 70 illustrated in FIG. 17, the intersection line 30*f* overlaps the range 21*b* equivalent to the effective visual field 21B and the portion outside the range 21*b*. Also, the scales 70A are displayed on the portion of the intersection line 30*f* overlapping the range 21*b*, and scales 70*aa* are displayed on the portion of the intersection line 30*f* overlapping the portion outside the range 21*b*. In addition, the range 21*b* is not displayed on the display unit 7 and is illustrated only for description.

The scales 70*aa* are displayed, for example, in a color different from that of the scales 70A, or are displayed in a line type (for example, a broken line) different from the scales 70A.

According to this configuration, the user can recognize which portion of the intersection line 30*f* is outside the effective visual field 21B depending on the difference in the display form of the scales. For this reason, measurement can be prevented from being performed by the scales 70*aa* in a large distortion range, and a measurement error can be prevented.

SIXTH MODIFICATION EXAMPLE

Figure 18:
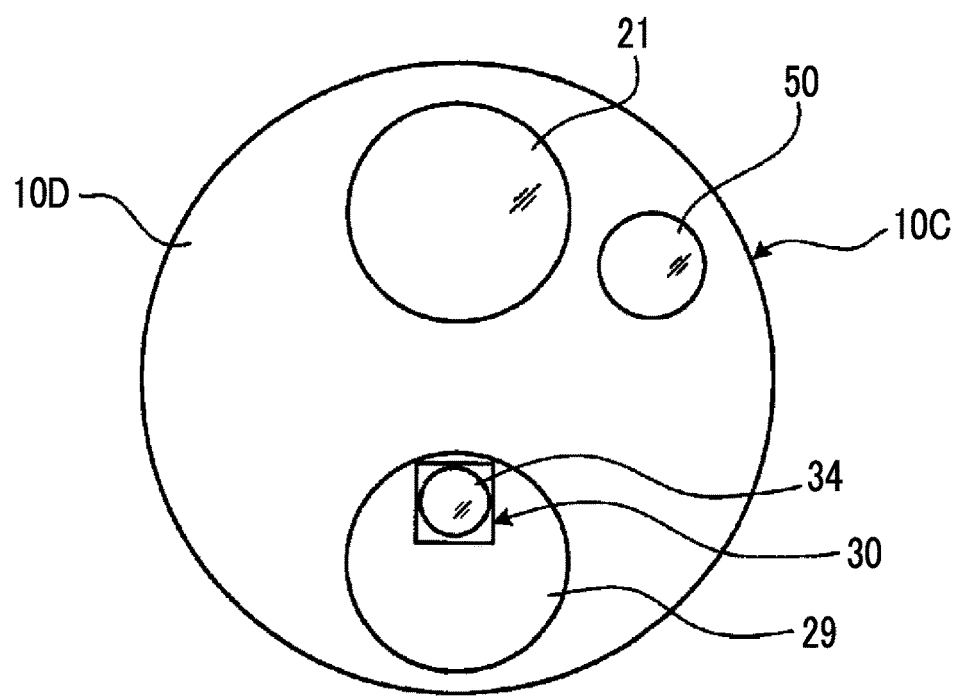
FIG. 18 is a view illustrating the configuration of a distal end surface 10D of the distal end part 10C of the endoscope device 100 of a sixth modification example.

The auxiliary measurement light emitting unit 30 of the endoscope device 100 may be attachable and detachable without being fixed to the distal end part 10C of the endoscope 1. For example, as illustrated in FIG. 18, a configuration in which the auxiliary measurement light emitting unit 30 can be post-attached to the opening 29 of the distal end part 10C as an accessory can be adopted. According to this configuration, it is possible to add a new function to the existing endoscope.

SEVENTH MODIFICATION EXAMPLE

The display control unit 43 may handle a direction in which the intersection line 30*f* included in the captured image in a case where the subject H1 is imaged extend as the vertical direction of the captured image. In this case, as the distance of the subject from the distal end part of the objective lens 21 changes, the intersection line 30*f* that is displayed on the display unit 7 and extends in the vertical direction moves in the horizontal direction on the captured image.

EIGHTH MODIFICATION EXAMPLE

Figure 19:
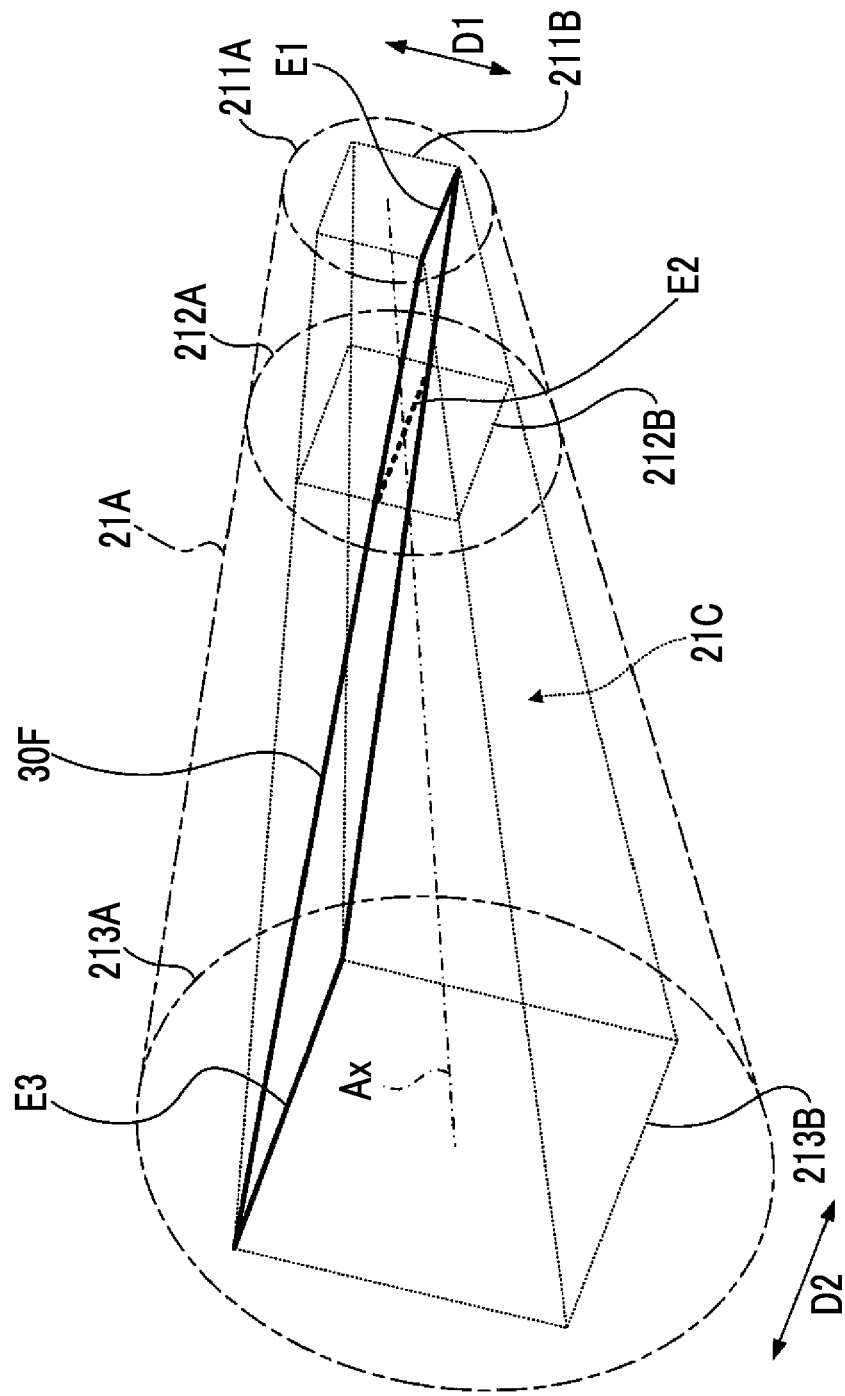
FIG. 19 is a perspective view illustrating a relationship between the visual field 21A and the effective imaging range 21C in the endoscope device 100 of an eighth modification example, and the plane 30F formed by the auxiliary measurement light 30A.

As illustrated in FIG. 6, the plane 30F formed by the auxiliary measurement light 30A also intersects the range of the visual field 21A outside the effective visual field 21B (effective imaging range 21C). However, as illustrated in FIG. 19, the DOE 32 may be designed such that the plane 30F intersects only the effective visual field 21B.

Figure 20:
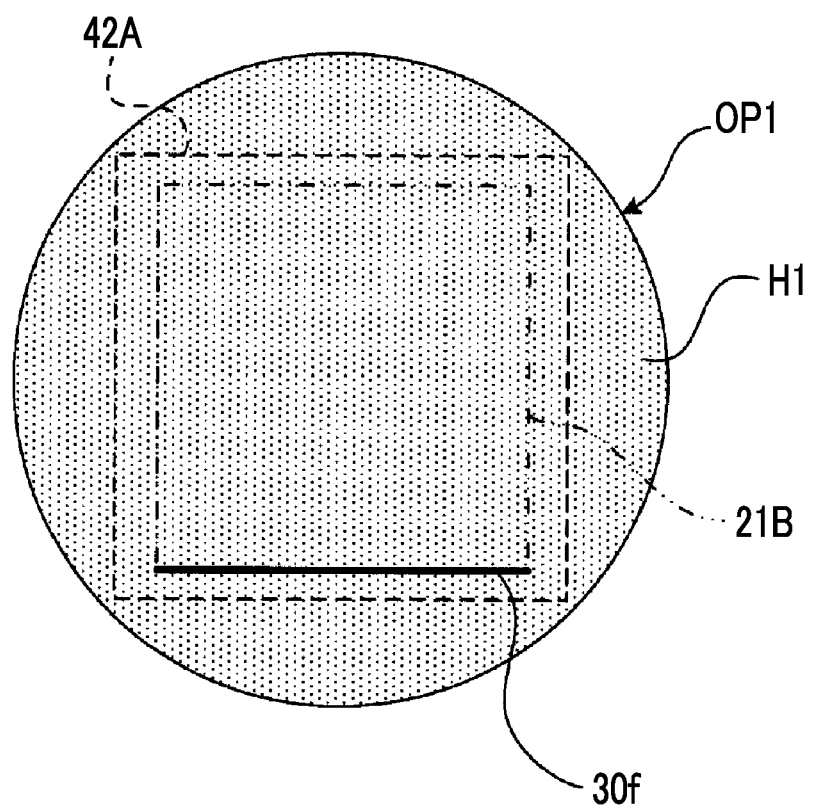
FIG. 20 is a view illustrating an example of an optical image formed by the imaging optical system of the endoscope device 100 of an eighth modification example.

In this case, for example, the optical image OP1 illustrated in FIG. 7 is changed to that illustrated in FIG. 20. That is, in the horizontal direction of the captured image, the intersection line 30*f* is displayed only on the range that is not influenced by the distortion. Therefore, measurement of the object to be observed can be performed with high accuracy by the scales on the intersection line 30*f*.

By combining the eighth modification example and the second modification example (FIG. 14) or third modification example (FIG. 15), generation of a measurement error can be further prevented.

In the description so far, although the example of the flexible endoscope has been shown as the endoscope 1, the invention can also be similarly applied to a hard endoscope.

As described above, the following matters are disclosed in the present specification.

(1) An endoscope device comprising an imaging optical system including an objective lens disposed at a distal end part of an endoscope; an imaging element that images a subject through the imaging optical system; a signal processing unit that processes a captured image signal obtained by imaging the subject by the imaging element to generate a captured image; an auxiliary measurement light emitting unit that emits planar auxiliary measurement light from the distal end part; and a display control unit that causes a display unit to display the captured image including an intersection line between the auxiliary measurement light and the subject that is formed in a portion where a plane formed by the auxiliary measurement light intersects the subject, the auxiliary measurement light emitting unit emitting the auxiliary measurement light in a state where the plane and an optical axis of the objective lens intersect each other at one specific point on the optical axis, and a distance of the one specific point from a distal end part of the objective lens being 5 mm or more and 20 mm or less.

(2) The endoscope device according to (1) in which the plane formed by the planar auxiliary measurement light that passes through an end part of an effective imaging range on the objective lens side and on one side in a vertical direction perpendicular to the optical axis, and passes through an end part of the effective imaging range on a side opposite to the objective lens side and on the other side in the vertical direction, the effective imaging range being an overlapping range between an effective visual field determined in advance in a visual field of the imaging optical system and a depth of field of the imaging optical system.

(3) The endoscope device according to (2) in which the display control unit causes the captured image to be displayed using a direction in which the intersection line included in the captured image in a case where a subject of which a distance from the distal end part of the objective lens is uniform is imaged extends, as a horizontal direction or vertical direction of the captured image.

(4) The endoscope device according to any one of (1) to (3) in which the display control unit causes a scale serving as an index of a size of the subject to be displayed on the intersection line included in the captured image.

(5) The endoscope device according to (4) in which the display control unit adds information indicating an effective visual field determined in advance in a visual field of the imaging optical system to the captured image to display the information.

(6) The endoscope device according to (4) in which the display control unit causes the scale not to be displayed in a case where the entire intersection line overlaps a portion of the captured image outside an effective visual field determined in advance in a visual field of the imaging optical system.

(7) The endoscope device according to (4) in which, in a case where the entire intersection line overlaps a portion of the captured image outside an effective visual field determined in advance in a visual field of the imaging optical system, the display control unit changes a display state of the scale compared to a case where the intersection line overlaps a portion of the captured image in the effective visual field.

(8) The endoscope device according to (4) in which, in a case where in the captured image, the intersection line overlaps a portion of an effective visual field determined in advance in a visual field of the imaging optical system and a portion of an outside of the effective visual field, the display control unit causes the scale of a portion of the intersection line overlapping the portion of the outside of the effective visual field not to be displayed.

(9) The endoscope device according to (4) in which, in a case where in the captured image, the intersection line overlaps a portion of an effective visual field determined in advance in a visual field of the imaging optical system and a portion of an outside of the effective visual field, the display control unit causes the scale of a portion of the intersection line overlapping the portion of the outside of the effective visual field to be displayed in a display form different from a display form of the scale of a portion of the intersection line overlapping the portion of the effective visual field.

(10) A measurement support method comprising a signal processing step of processing a captured image signal, which is obtained by imaging a subject by an imaging element through an imaging optical system including an objective lens disposed at a distal end part of an endoscope, to generate a captured image; an auxiliary measurement light emission control step of causing planar auxiliary measurement light to be emitted from the distal end part; and a display control step of causing a display unit to display the captured image including an intersection line between the auxiliary measurement light and the subject that is formed in a portion where a plane formed by the auxiliary measurement light intersects the subject, in the auxiliary measurement light emission control step, the auxiliary measurement light being caused to be emitted from the distal end part in a state where an optical axis of the objective lens and the plane intersect each other at one specific point on the optical axis, and a distance of the one specific point from a distal end part of the objective lens is 5 mm or more and 20 mm or less.

From the above description, an endoscope device according to the following Annex 1 can be ascertained.

[Annex 1] An endoscope device comprising:

an imaging optical system comprising an objective lens disposed at a distal end part of an endoscope;

an imaging element that images a subject through the imaging optical system;

an auxiliary measurement light emitting unit that emits planar auxiliary measurement light from the distal end part; and a processor, wherein the processor configured to process a captured image signal obtained by imaging a subject by the imaging element to generate a captured image, and cause a display unit to display the captured image including an intersection line between the auxiliary measurement light and the subject that is formed in a portion where a plane formed by the auxiliary measurement light intersects the subject, and wherein the auxiliary measurement light emitting unit emitting the auxiliary measurement light in a state where the plane and an optical axis of the objective lens intersect each other at one specific point on the optical axis, and a distance of the one specific point from a distal end part of the objective lens being 5 mm or more and 20 mm or less.

EXPLANATION OF REFERENCES

100: endoscope device
1: endoscope
2: body part
10: insertion Part
10A: flexible part
10B: bending part
10C: distal end part
10D: distal end surface
11: operating part
12: angle knob
13: universal cord
13A, 13B: connector part
6: input unit
7: display unit
21: objective lens
Ax: optical axis
22: lens group
23: imaging element
24: ADC
25: memory
26: communication interface
27: imaging control unit
29: opening
30: auxiliary measurement light emitting unit
30A: auxiliary measurement light
31: light source
32: DOE
33: prism
34: auxiliary measurement lens
4: control device
41: communication interface
42: signal processing unit
43: display control unit
44: system control unit
5: light source device
50: illumination lens
51: light source control unit
52: light source unit
53: light guide
60: air and water supply nozzle
D1: first direction
D2: second direction
D3: optical axis direction
L1: distance
R1: depth of field
21A: visual field
21B: effective visual field
21C: effective imaging range
P1, P2, P3: position
211A, 213A, 211B, 213B: end part
212A, 212B: cross-section
30F: plane
E1, E3: end part
E2: centerline
H1: subject OP1, OP2, OP3: optical image
30f: intersection line
42A: signal processing range
70: captured image
70A: scale
P: polyp
H: horizontal direction
V: vertical direction
70B: frame
21b: range equivalent to effective visual field
70a, 70aa: scale

What is claimed is:

1. An endoscope device comprising:
an imaging optical system including an objective lens disposed at a distal end part of an endoscope; and
a processor, wherein the processor is configured to:
   image a subject through the imaging optical system;
   process a captured image signal obtained by imaging the subject by the imaging element to generate a captured image;
   emit, from an auxiliary measurement light emitting unit, planar auxiliary measurement light from the distal end part; and
   display the captured image including an intersection line between the auxiliary measurement light and the subject that is formed in a portion where a plane formed by the auxiliary measurement light intersects the subject,
the auxiliary measurement light is emitted in a state where the plane and an optical axis of the objective lens intersect each other at one specific point on the optical axis, and
a distance of the one specific point from a distal end part of the objective lens is 5 mm or more and 20 mm or less.

2. The endoscope device according to claim 1, wherein the planar auxiliary measurement light passes through an end part of an effective imaging range on the objective lens side and on one side in a vertical direction perpendicular to the optical axis, and passes through an end part of the effective imaging range on a side opposite to the objective lens side and on the other side in the vertical direction, the effective imaging range being an overlapping range between an effective visual field determined in advance in a visual field of the imaging optical system and a depth of field of the imaging optical system.

3. The endoscope device according to claim 2, wherein the processor is configured to cause the captured image to be displayed using a direction in which the intersection line included in the captured image in a case where a subject of which a distance from the distal end part of the objective lens is uniform is imaged extends, as a horizontal direction or vertical direction of the captured image.

4. The endoscope device according to claim 1, wherein the processor is configured to cause a scale serving as an index of a size of the subject to be displayed on the intersection line included in the captured image.

5. The endoscope device according to claim 2, wherein the processor is configured to cause a scale serving as an index of a size of the subject to be displayed on the intersection line included in the captured image.

6. The endoscope device according to claim 3, wherein the processor is configured to cause a scale serving as an index of a size of the subject to be displayed on the intersection line included in the captured image.

7. The endoscope device according to claim 4, wherein the processor is configured to add information indicating an effective visual field determined in advance in a visual field of the imaging optical system to the captured image to display the information.

8. The endoscope device according to claim 5, wherein the processor is configured to add information indicating the effective visual field determined in advance in the visual field of the imaging optical system to the captured image to display the information.

9. The endoscope device according to claim 6, wherein the processor is configured to add information indicating the effective visual field determined in advance in the visual field of the imaging optical system to the captured image to display the information.

10. The endoscope device according to claim 4, wherein the processor is configured to cause the scale not to be displayed in a case where the entire intersection line overlaps a portion of the captured image outside an effective visual field determined in advance in a visual field of the imaging optical system.

11. The endoscope device according to claim 5, wherein the processor is configured to cause the scale not to be displayed in a case where the entire intersection line overlaps a portion of the captured image outside the effective visual field determined in advance in the visual field of the imaging optical system.

12. The endoscope device according to claim 6, wherein the processor is configured to cause the scale not to be displayed in a case where the entire intersection line overlaps a portion of the captured image outside the effective visual field determined in advance in the visual field of the imaging optical system.

13. The endoscope device according to claim 4, wherein, in a case where the entire intersection line overlaps a portion of the captured image outside an effective visual field determined in advance in a visual field of the imaging optical system, the processor is further configured to change a display state of the scale compared to a case where the intersection line overlaps a portion of the captured image in the effective visual field.

14. The endoscope device according to claim 5, wherein, in a case where the entire intersection line overlaps a portion of the captured image outside the effective visual field determined in advance in the visual field of the imaging optical system, the processor is further configured to change a display state of the scale compared to a case where the intersection line overlaps a portion of the captured image in the effective visual field.

15. The endoscope device according to claim 6, wherein, in a case where the entire intersection line overlaps a portion of the captured image outside the effective visual field determined in advance in the visual field of the imaging optical system, the processor is further configured to change a display state of the scale compared to a case where the intersection line overlaps a portion of the captured image in the effective visual field.

16. The endoscope device according to claim 4, wherein, in a case where in the captured image, the intersection line overlaps a portion of an effective visual field determined in advance in a visual field of the imaging optical system and a portion of an outside of the effective visual field, the processor is further configured to cause the scale of a portion of the intersection line overlapping the portion of the outside of the effective visual field not to be displayed.

17. The endoscope device according to claim 5, wherein, in a case where in the captured image, the intersection line overlaps a portion of the effective visual field determined in advance in the visual field of the imaging optical system and a portion of an outside the effective visual field, the processor is further configured to cause the scale of a portion of the intersection line overlapping the portion of the outside of the effective visual field not to be displayed.

18. The endoscope device according to claim 4, wherein, in a case where in the captured image, the intersection line overlaps a portion of an effective visual field determined in advance in a visual field of the imaging optical system and a portion of an outside of the effective visual field, the processor is further configured to cause the scale of a portion of the intersection line overlapping the portion of the outside of the effective visual field to be displayed in a display form different from a display form of the scale of a portion of the intersection line overlapping the portion of the effective visual field.

19. A measurement support method using the endoscope device according to claim 1, the method comprising:
processing the captured image signal, which is obtained by imaging the subject by the imaging element through the imaging optical system including the objective lens disposed at the distal end part of the endoscope, to generate the captured image;
causing the planar auxiliary measurement light to be emitted from the distal end part; and
causing the display unit to display the captured image including the intersection line between the auxiliary measurement light and the subject that is formed in the portion where the plane formed by the auxiliary measurement light intersects the subject, wherein,
the auxiliary measurement light is emitted from the distal end part in a state where the optical axis of the objective lens and the plane intersect each other at one specific point on the optical axis, and
the distance of the one specific point from the distal end part of the objective lens is 5 mm or more and 20 mm or less.

20. An endoscope device comprising:
an imaging optical system comprising an objective lens disposed at a distal end part of an endoscope;
an imaging element that images a subject through the imaging optical system;
an auxiliary measurement light emitting unit that emits a planar auxiliary measurement light from the distal end part; and
a processor, wherein the processor is configured to
process a captured image signal obtained by imaging a subject by the imaging element to generate a captured image, and
cause a display to display the captured image including an intersection line between the auxiliary measurement light and the subject that is formed in a portion where a plane formed by the auxiliary measurement light intersects the subject, and
the auxiliary measurement light is emitted in a state where the plane and an optical axis of the objective lens intersect each other at one specific point on the optical axis, and
a distance of the one specific point from a distal end part of the objective lens being 5 mm or more and 20 mm or less.

21. The endoscope device according to claim 1, further comprising
an illumination lens disposed at the distal end part of the endoscope, wherein
the processor is configured to image the subject through the imaging optical system in a state where illumination light is emitted to the subject through the illumination lens.

22. The measurement support method according to claim 19, wherein
the captured image signal is obtained by imaging the subject by the imaging element through the imaging optical system including the objective lens in a state where illumination light is emitted to the subject through an illumination lens disposed at the distal end part of the endoscope.

23. The endoscope device according to claim 20, further comprising
an illumination lens disposed at the distal end part of the endoscope, wherein
the imaging element images the subject through the imaging optical system in a state where illumination light is emitted to the subject through the illumination lens.

* * * * *